United States Patent
Chatterjee et al.

(10) Patent No.: US 12,276,715 B2
(45) Date of Patent: Apr. 15, 2025

(54) SYSTEMS AND METHODS FOR MOTION-ARTIFACT REDUCTION IN MAGNETIC RESONANCE IMAGING

(71) Applicant: GE Precision Healthcare LLC, Wauwatosa, WI (US)

(72) Inventors: Sudhanya Chatterjee, Karnataka (IN); Megha Goel, Karnataka (IN); Suresh Emmanuel Devadoss Joel, Karnataka (IN); Rohan Keshav Patil, Karnataka (IN); Florintina C, Karnataka (IN); Preetham Shankapal, Karnataka (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 209 days.

(21) Appl. No.: 18/331,885

(22) Filed: Jun. 8, 2023

(65) Prior Publication Data
US 2024/0410965 A1    Dec. 12, 2024

(51) Int. Cl.
*G01R 33/48*    (2006.01)
*A61B 5/055*    (2006.01)
(Continued)

(52) U.S. Cl.
CPC .......... *G01R 33/4824* (2013.01); *A61B 5/055* (2013.01); *G01R 33/5608* (2013.01);
(Continued)

(58) Field of Classification Search
CPC ............ G01R 33/4824; G01R 33/5608; G01R 33/56509; A61B 5/055; G06T 2207/10088; G06T 2207/20081
See application file for complete search history.

(56) References Cited

U.S. PATENT DOCUMENTS 9,103,898 B2 *   8/2015  Holmes .............. G01R 33/5602
11,187,769 B2 * 11/2021  Splitthoff ........... G01R 33/5608
(Continued)

OTHER PUBLICATIONS

Haskell, M. et al., "Network Accelerated Motion Estimation and Reduction (NAMER): Convolutional neural network guided retrospective motion correction using a separable motion model," Magnetic Resonance in Medicine, vol. 82, No. 4, Oct. 2019, Available Online May 2, 2019, 10 pages.
(Continued)

*Primary Examiner* — Gregory H Curran
(74) *Attorney, Agent, or Firm* — McCoy Russell LLP

(57) ABSTRACT

Systems and methods are provided for reconstructing images from motion-affected k-space data. In one example, a method comprises obtaining k-space data of a spin echo magnetic resonance imaging (MRI) exam of a subject, the k-space data comprising a plurality of echo train lengths (ETLs), with each ETL comprising a subset of lines of the k-space data. The method further comprises identifying a subset of ETLs of the plurality of ETLs of the k-space data corresponding to a dominant pose of the subject, generating an undersampled version of the k-space data, the undersampled version including only the subset of ETLs, entering the undersampled version of the k-space data as input to a reconstruction model trained to output a reconstructed image based on the undersampled version of the k-space data, and displaying the reconstructed image on a display device and/or saving the reconstructed image in memory.

20 Claims, 12 Drawing Sheets

(51) Int. Cl.
  *G01R 33/56* (2006.01)
  *G01R 33/565* (2006.01)
  *G06T 7/00* (2017.01)

(52) U.S. Cl.
  CPC ...... *G01R 33/56509* (2013.01); *G06T 7/0012* (2013.01); *G06T 2207/10088* (2013.01); *G06T 2207/20081* (2013.01)

(56) References Cited

U.S. PATENT DOCUMENTS

| | | | |
|---|---|---|---|
| 2020/0337591 A1 | 10/2020 | Rotman et al. | |
| 2020/0337592 A1 | 10/2020 | Brada et al. | |
| 2022/0128640 A1* | 4/2022 | Chatterjee | G01R 33/4818 |

OTHER PUBLICATIONS

Runge, V. et al., "Motion in Magnetic Resonance: New Paradigms for Improved Clinical Diagnosis," Investigative Radiology, vol. 54, No. 7, Jul. 2019, 13 pages.

Shen, D. et al., "Medical Image Computing and Computer Assisted Intervention—MICCAI 2019," Proceedings of the 22nd International Conference, Oct. 13, 2019, Shenzhen, China, 837 pages.

Rotman, M. et al., "A Novel Approach for Correcting Multiple Discrete Rigid In-Plane Motions Artefacts in MRI Scans," ArXiv Cornell University Website, Available Online at https://arxiv.org/abs/2006.13804, Available as Early as Jun. 29, 2020, 7 pages.

Jansen, I. et al., "A deep network for continuous motion detection during MRI scanning," Proceedings of the ISMRM & SMRT Virtual Conference & Exhibition, Available Online at https://cds.ismrm.org/protected/20MProceedings/PDFfiles/3364.html, Aug. 8, 2020, 3 pages.

Brada, R. et al., "Perceptual motion scoring: An algorithm for automated detection and grading of MRI motion artifacts," Proceedings of the ISMRM & SMRT Annual Meeting & Exhibition Website, Available Online at https://www.ismrm.org/21/program-files/TeaserSlides/TeasersPresentations/1366-Teaser.html, May 15, 2021, Virtual Meeting, 1 page.

Hossbach, J. et al., "Deep learning-based motion quantification from k-space for fast model-based magnetic resonance imaging motion correction," Medical Physics, vol. 50, No. 4, Apr. 2023, Available Online Dec. 13, 2022, 15 pages.

* cited by examiner

SYSTEMS AND METHODS FOR MOTION-ARTIFACT REDUCTION IN MAGNETIC RESONANCE IMAGING

TECHNICAL FIELD

The present description relates generally to medical imaging. More specifically, the present disclosure relates to motion-artifact reduction in magnetic resonance imaging.

BACKGROUND

Magnetic resonance imaging (MRI) is a medical imaging modality that can create images of the inside of a human body without using x-rays or other ionizing radiation. A MRI scan typically includes a series of radiofrequency (RF) excitation pulses and magnetic field gradient pulses that are played out with specific timings and in a specific sequence to prepare contrast and encode spatial information into the signal to generate an image. MRI scans may be relatively time-consuming and as such are prone to motion-related image artifacts.

BRIEF DESCRIPTION

In one example, a method includes obtaining k-space data of a subject, the k-space data comprising a plurality of echo train lengths (ETLs), each ETL comprising a subset of lines of the k-space data, identifying a subset of ETLs of the plurality of ETLs of the k-space data corresponding to a dominant pose of the subject, generating an undersampled version of the k-space data, the undersampled version including only the subset of ETLs, entering the undersampled version of the k-space data as input to a reconstruction model trained to output a reconstructed image based on the undersampled version of the k-space data, and displaying the reconstructed image on a display device and/or saving the reconstructed image in memory.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to reconstructing images based on an undersampled k-space generated by removing motion-affected k-space echo train lengths (ETLs) and/or k-space ETLs of one or more non-dominant poses of a subject. In particular, systems and methods are provided for identifying a dominant pose of the subject based on identified motion-affected k-space ETLs and one or more non-dominant poses, removing the k-space ETLs corresponding to the one or more non-dominant poses to generate an undersampled k-space, and reconstructing one or more images based on the undersampled k-space.

Motion is one of the leading causes of scan recalls and non-diagnostic MR images. It has been found that a quarter of unanticipated events in MR scans are due to motion. Hence, the presence of motion during an MR scan may increase scan cost and presents risk of missing a diagnosis or misdiagnosis. Motion artifacts might occur due to symptoms of patients because of which they are unable to remain still inside the MRI scanner, long scan times (leading to permanent/momentary change in pose), etc. Motion artifacts have a high chance of rendering an MR image non-diagnostic.

The embodiments disclosed herein resolve the above-described issues with a system wherein motion-affected k-space ETLs of k-space data of an imaging subject (e.g., patient) are identified and used to distinguish a dominant pose of the subject from the one or more non-dominant poses, the k-space ETLs corresponding to the one- or more non-dominant poses are removed from the k-space data, forming the undersampled k-space data, and a reconstruction of one or more images is performed using a reconstruction model. The reconstruction model may be a deep learning model trained in a manner to reconstruct images from undersampled k-space data, wherein the reconstruction model is trained with training k-space data where arbitrary ETLs are dropped from the training k-space data.

Figure 1:
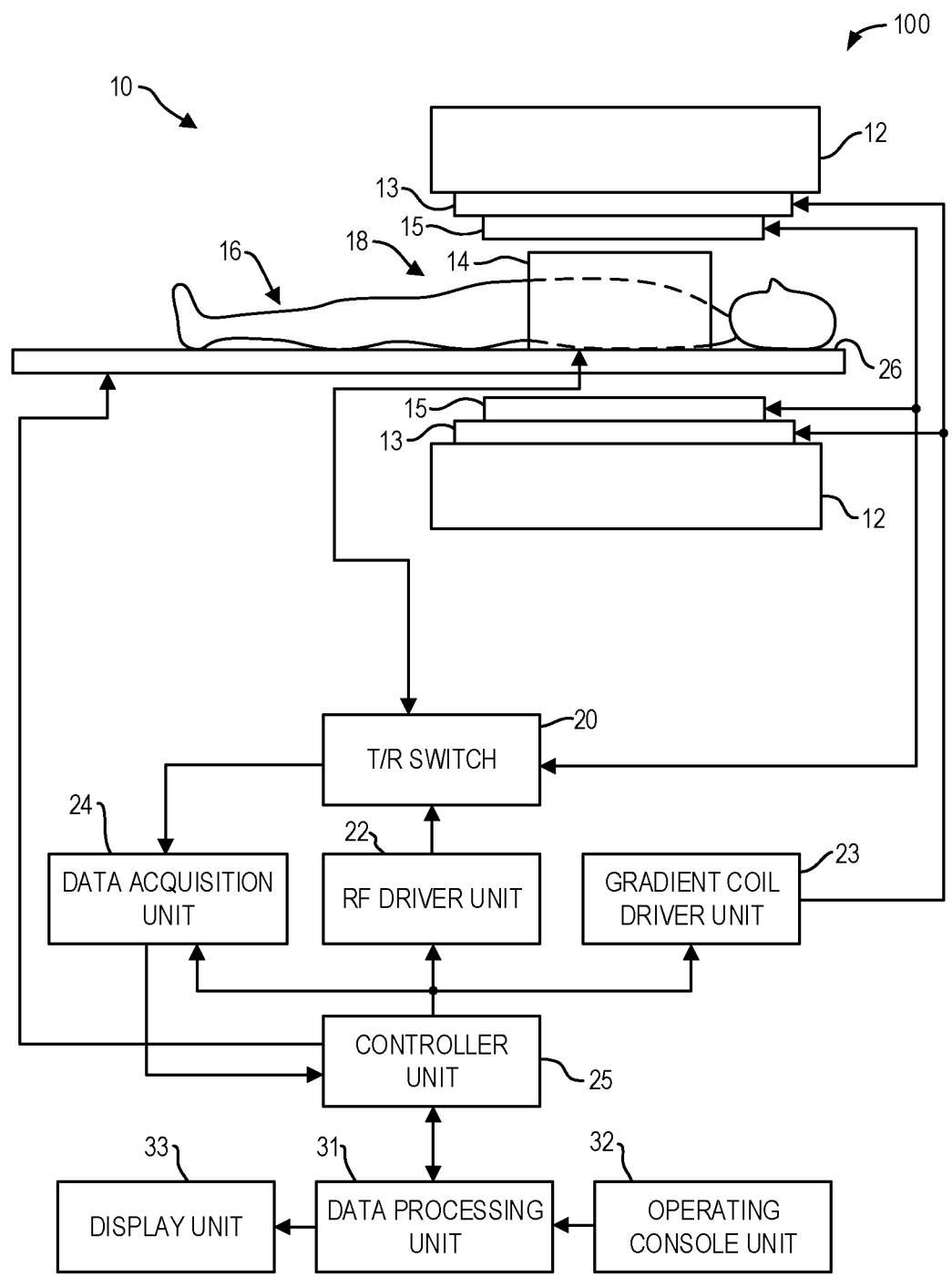
FIG. 1 is a block diagram of an MRI system according to an embodiment of the disclosure.
Figure 2:
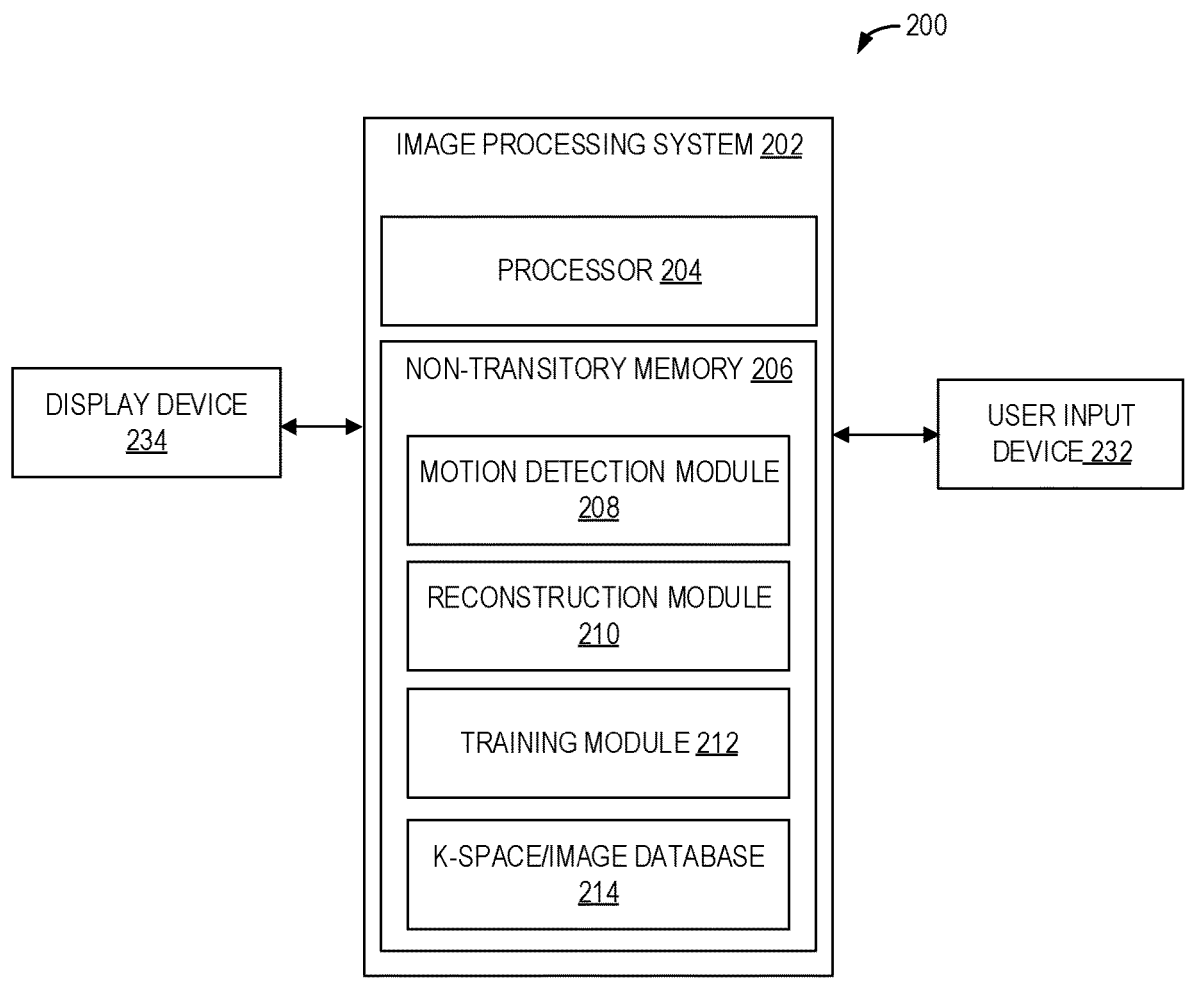
FIG. 2 schematically shows an example image processing system.
Figure 3:
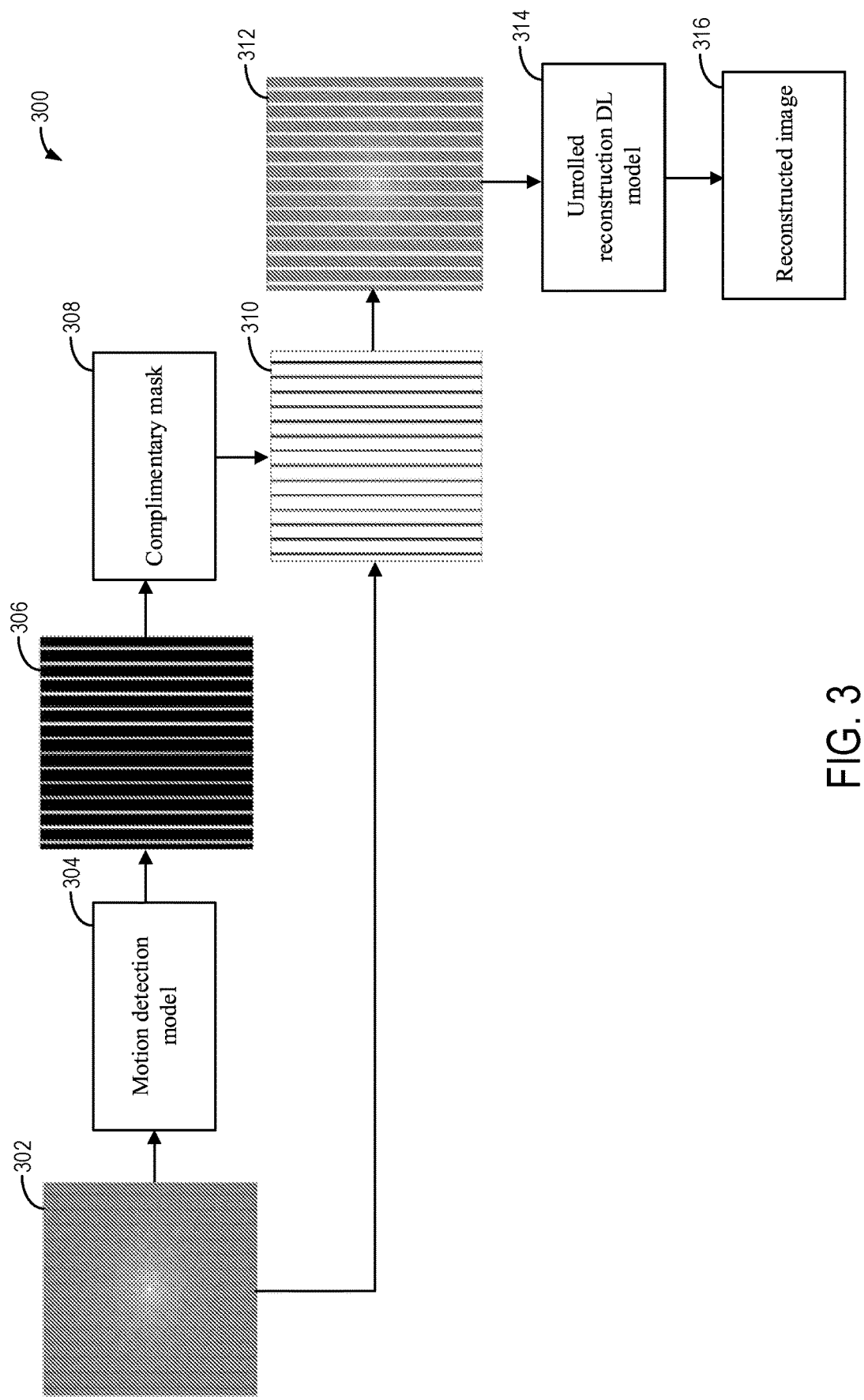
FIG. 3 schematically shows an example process for detecting motion-affected k-space data and reconstructing an image from k-space data with the motion-affected k-space data removed, using a reconstruction model.
Figure 4:
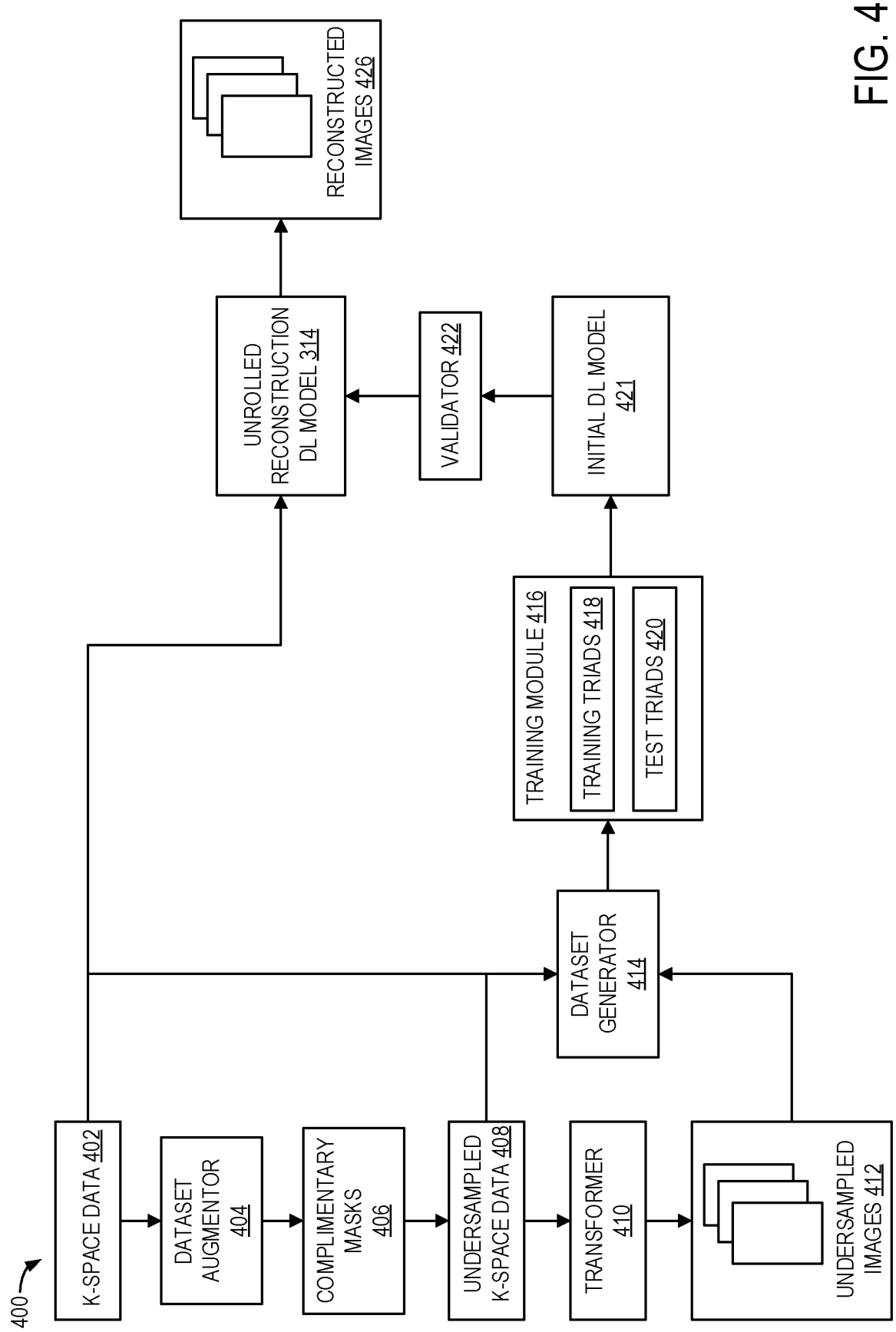
FIG. 4 schematically illustrates an example process for training a reconstruction model to reconstruct images from k-space data with motion-affected k-space data removed.
Figure 5:
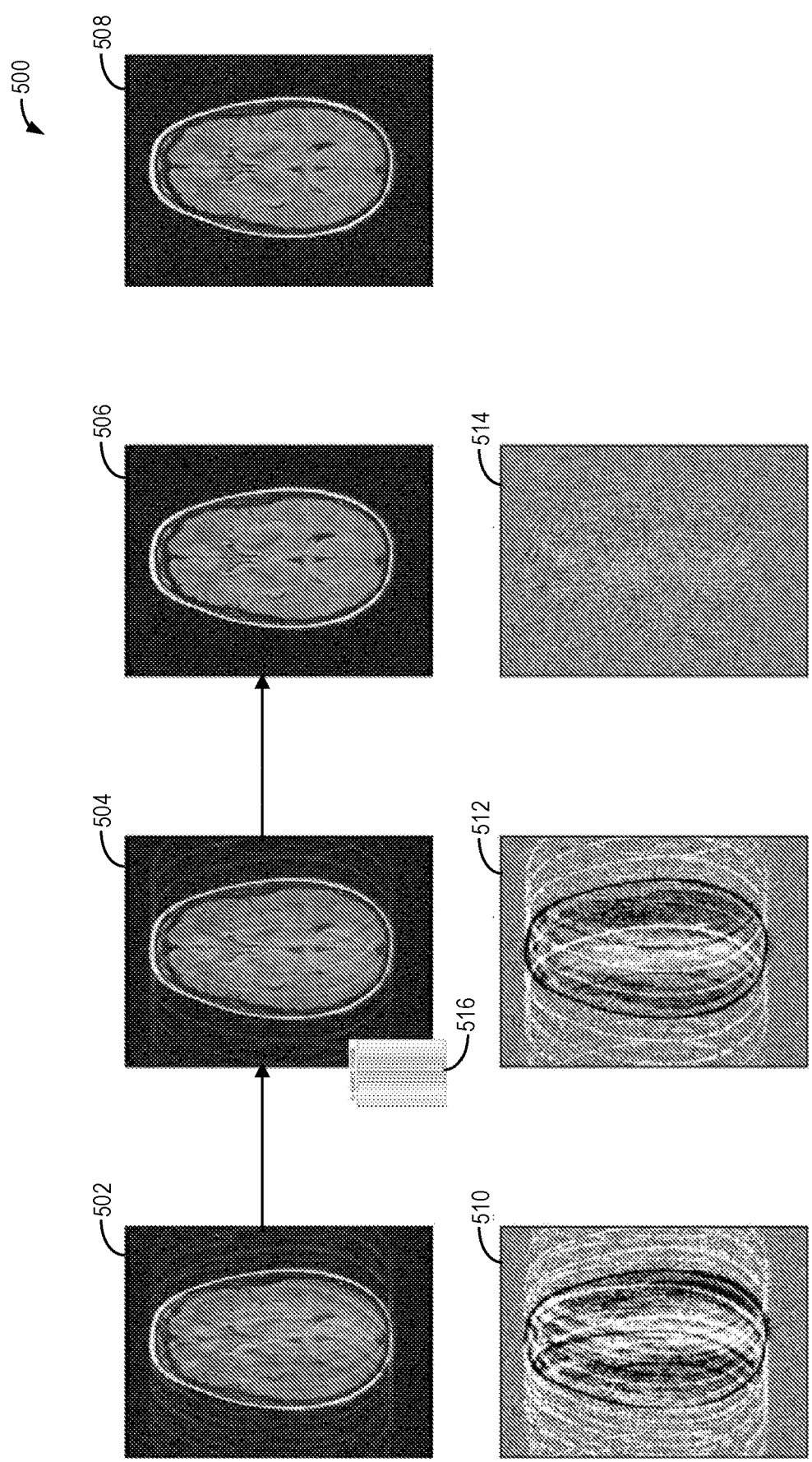
FIGS. 5-7 show example images reconstructed from motion-affected k-space data.
Figure 6:
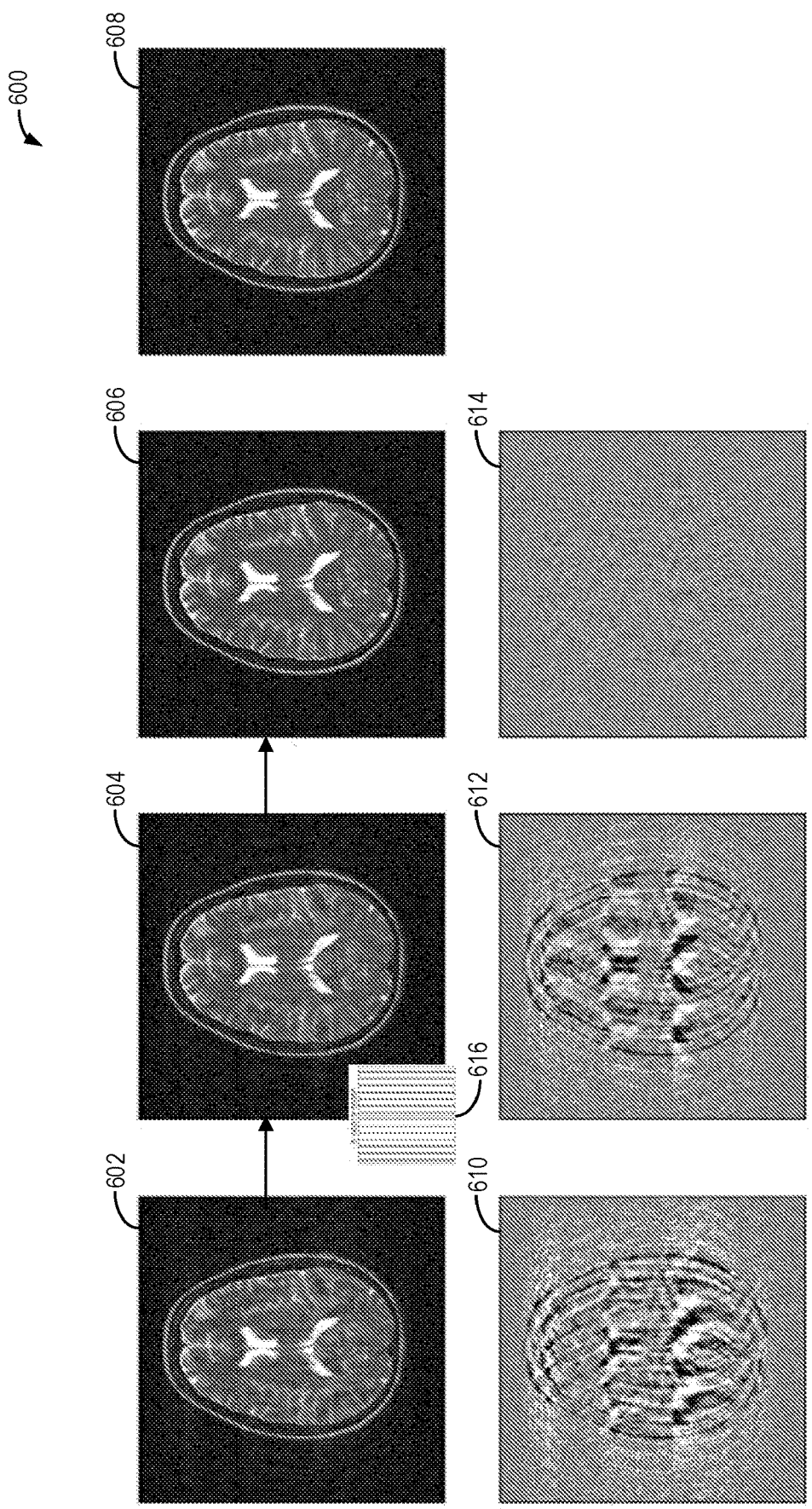
Figure 7:
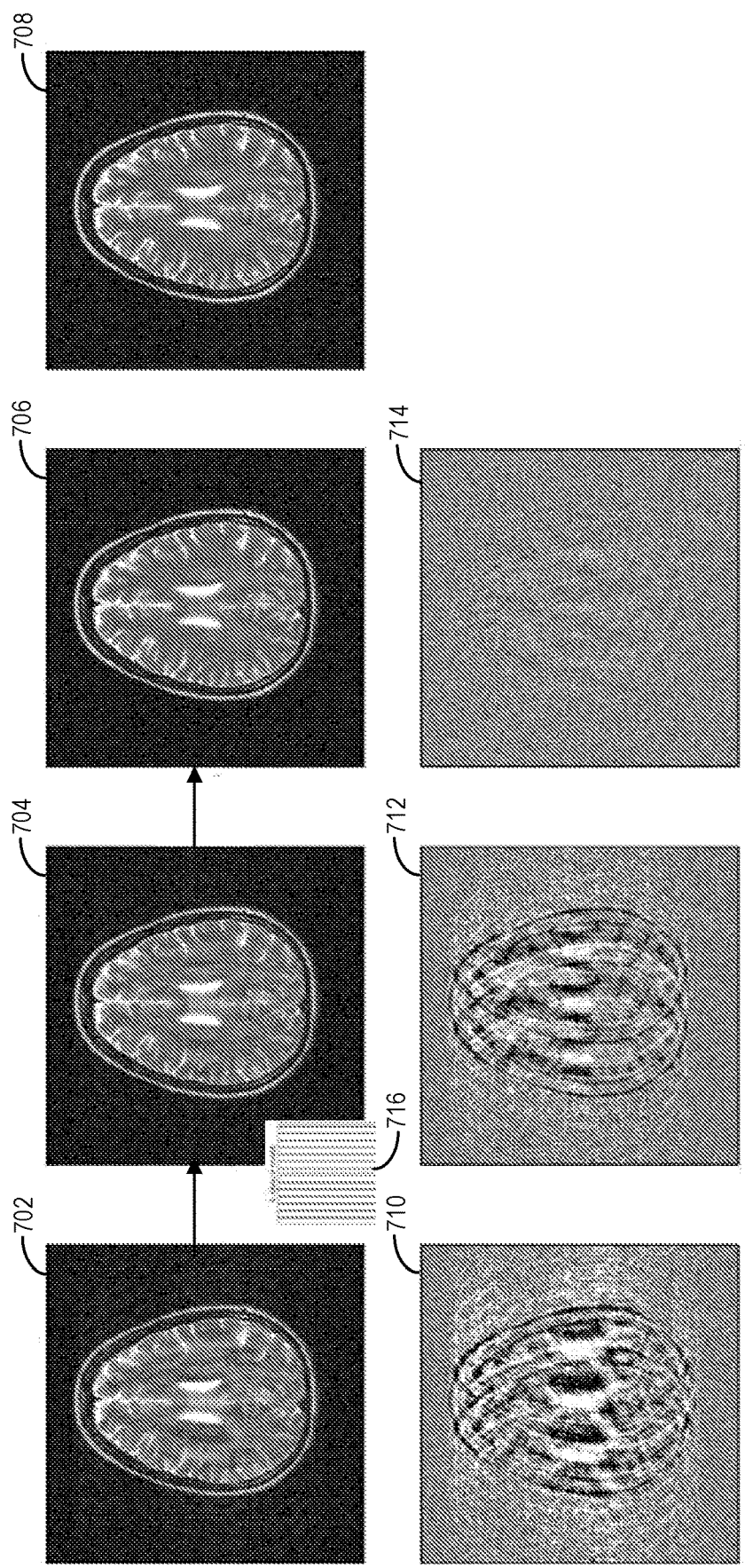
Figure 8:
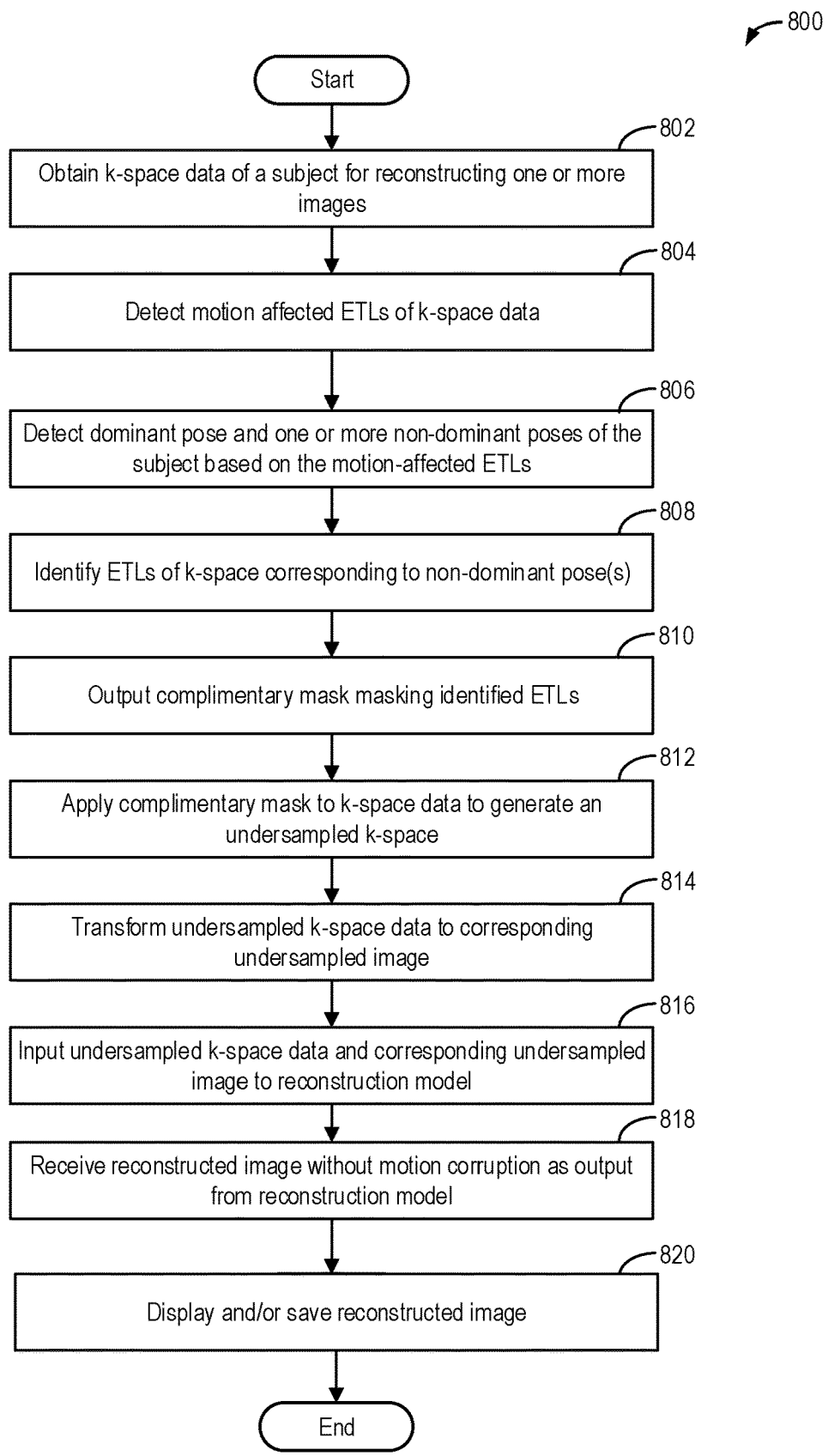
FIG. 8 is a flow chart illustrating an example method for deploying a reconstruction model to reconstruct an image based on an undersampled k-space dataset.
Figure 9:
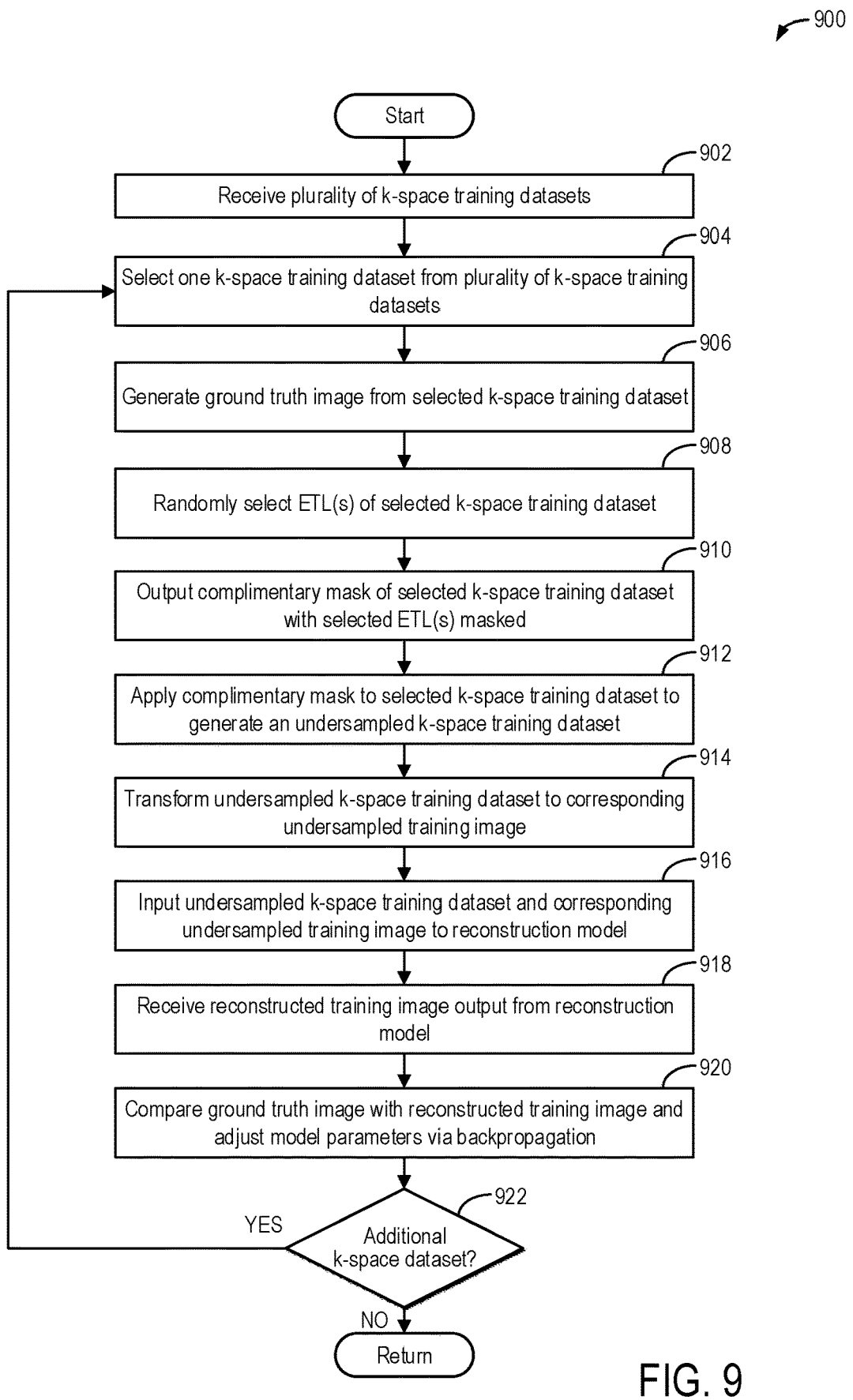
FIG. 9 is a flow chart illustrating an example method for training a reconstruction model to reconstruct an image based on an undersampled k-space dataset.
Figure 10:
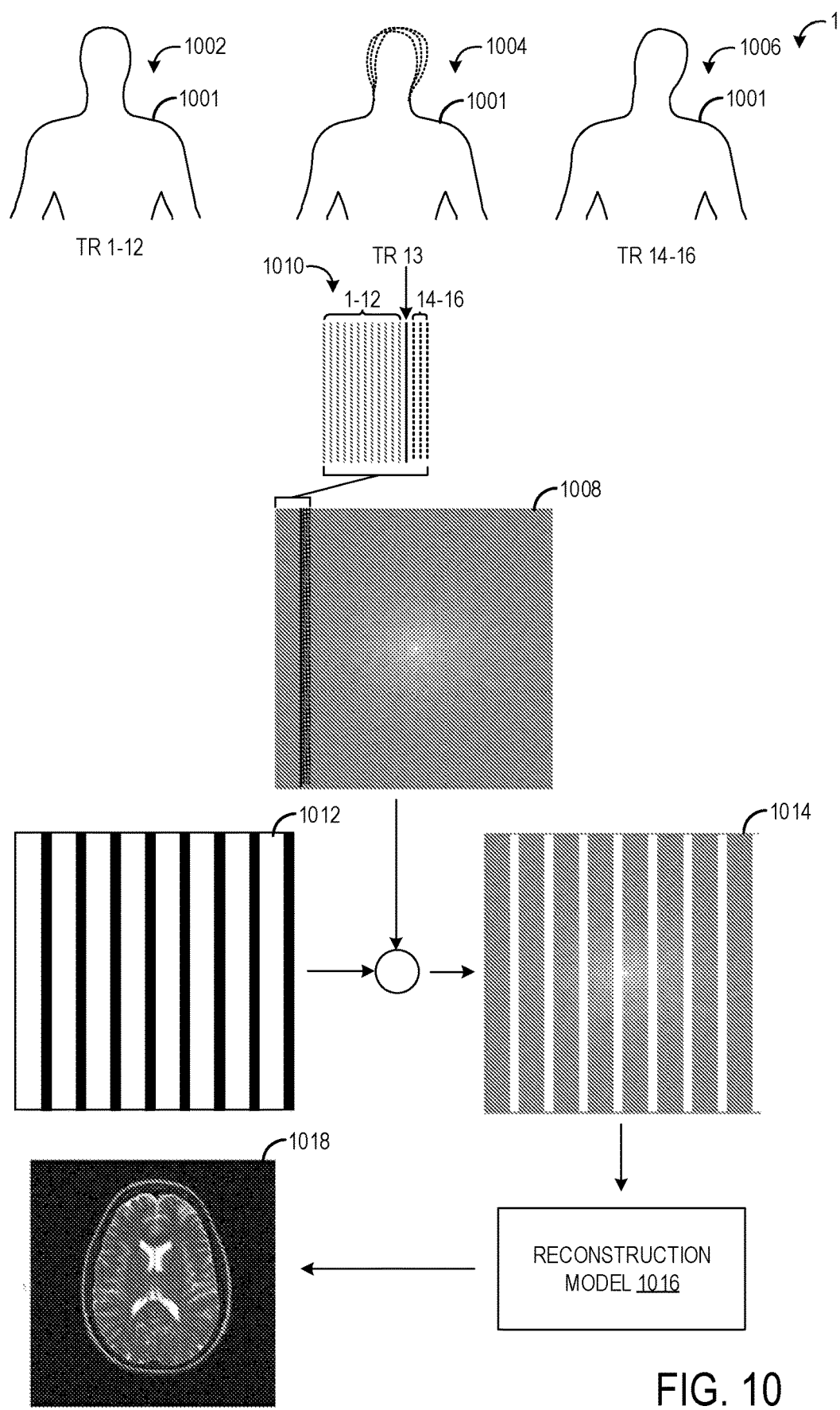
FIG. 10 schematically illustrates an example process for reducing motion-based artifacts using a reconstruction model.

An example of an MRI system that may obtain k-space data used in the image reconstruction process is shown in FIG. 1. An example of an image processing system that performs the image reconstruction process according to the embodiments described herein is shown in FIG. 2. FIG. 3 shows an example process for performing the image reconstruction process using k-space data wherein motion-affected k-space ETLs and k-space ETLs corresponding to one or more non-dominant poses are removed as input to a reconstruction model. An example process for training the reconstruction model is shown in FIG. 4. FIGS. 5-7 show that artifact-free or reduced-artifact images may be reconstructed with the disclosed reconstruction model. An example method for deploying the reconstruction model is shown in FIG. 8. An example method for training the reconstruction model is shown in FIG. 9. FIG. 10 schematically shows an example process for reconstructing images from undersampled k-space that may be carried out according to the method of FIG. 8.

FIG. 1 illustrates an MRI apparatus 10 that includes a magnetostatic field magnet unit 12, a gradient coil unit 13, an RF coil unit 14, an RF body coil unit 15 (e.g., volume coil unit), a transmit/receive (T/R) switch 20, an RF driver unit 22, a gradient coil driver unit 23, a data acquisition unit 24, a controller unit 25, a patient bed or table 26, a data processing unit 31, an operating console unit 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface of the RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF body coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF body coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF body coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) image of the subject 16 generated by the data processing unit 31.

During an MRI scan using the MRI apparatus 10, a subject may be positioned within the imaging space 18 and an acquisition protocol may be carried out to obtain MR signals of the subject. The acquisition protocol may include a plurality of pulse sequences where in each pulse sequence, contrast is prepared via one or more RF pulses applied by the RF body coil unit 15 and the gradient coil unit 13 is controlled to spatially encode the resultant MR signals. The spatially-encoded MR signals are received by the RF coil unit 14 are digitized and stored in k-space. Thus, k-space data or a k-space dataset may refer to the raw MR signals prior to processing into an image. In some examples, one line of k-space may be filled with the raw MR signals per pulse sequence (also referred to as repetition time). In other examples, one line of k-space may be filled with the raw MR signals per echo, where more than one echo is generated per pulse sequence/repetition time.

Referring to FIG. 2, image processing system 202 configured to receive and process k-space data is shown. In some embodiments, image processing system 202 is incorporated into the MRI apparatus 10. For example, image processing system 202 may be provided in the MRI apparatus 10 as data processing unit 31. In some embodiments, at least a portion of image processing system 202 is disposed at a device (e.g., edge device, server, etc.) communicably coupled to the MRI apparatus 10 via wired and/or wireless connections. In some embodiments, at least a portion of image processing system 202 is disposed at a separate device (e.g., a workstation) which can receive k-space data from the MRI system or from a storage device which stores the images/k-space data generated by the MRI system. Image processing system 202 may be operably/communicatively coupled to a user input device 232 and a display device 234. User input device 232 may be integrated into an MRI system, such as at user input device of the MRI apparatus 10. Similarly, display device 234 may be integrated into an MRI system, such as at display device of MRI apparatus 10.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, processor 204 may optionally include individual components that are distributed throughout two or more devices, which may be remotely located and/or configured for coordinated processing. In some embodiments, one or more aspects of processor 204 may be virtualized and executed by remotely-accessible networked computing devices configured in a cloud computing configuration.

Non-transitory memory 206 may store a motion detection module 208, a reconstruction module 210, a training module 212, and a k-space/image database 214. Motion detection module 208 may be configured to detect ETLs of k-space data that are affected by motion. In some examples, motion detection module 208 may include one or more machine learning (ML) models configured to identify motion-affected ETLs of k-space data and may include trained and/or untrained ML models, and may further include various data, or metadata pertaining to the one or more ML models stored therein. In other examples, motion detection module 208 may be configured to detect motion in k-space data using analytical methods or based on output received from one or more sensors of the MRI apparatus 10 (e.g., one or more cameras). Analytical methods may be applied on data acquired from a hardware system (e.g., sensors/cameras) to model the direction and extent of motion.

As an example, motion-affected ETLs may be detected by determining a normalized motion curve for a given MRI exam/scan, where the normalized motion curve is determined by reconstructing two single-coil images (e.g., one from coil 3 and one from coil 5) and determining the difference between the two images and going back to k-space and summing the difference in k-space along the readout direction to form a projected k-space difference. The projected k-space difference is averaged over slices and self-normalized, then summed over ETLs to obtain an overall motion curve (as a function of ETL index). The overall motion curve is separated into two parts (one for ETLs spread in the center of k-space and one for ETLs in the periphery of k-space) and the two parts are normalized separately to form a normalized motion curve that plots a difference sum as a function of ETL index. The area under the normalized motion curve can provide a motion estimate. Further, the normalized motion curve may be thresholded, such that ETLs that contribute the most to motion may be identified. The identified ETLs may then be mapped back to the phase-encoding line positions in k-space to generate a binary mask for masking the motion-affected ETLs, as explained in more detail below.

As another example, motion-affected ETLs may be identified using a machine learning model (e.g., deep learning model) trained to identify motion-affected ETLs based on sub-images created from pairs of ETLs. The model learns to detect image features that are different when motion is present between the pair of ETLs relative to when motion is not present between the ETLs.

Reconstruction module 210 may include a reconstruction model, which may be a ML model (e.g., a deep learning model), which may be configured to reconstruct images from k-space data. In some examples, the reconstruction model may be an unrolled deep learning model having a suitable architecture, such as deep learning unit as regularizer and a data consistency step (such as proximal mapping, alternating direction method of multipliers (ADMM), etc.). Reconstruction module 210 may include trained and/or untrained ML models, and may further include various data, or metadata pertaining to the one or more ML models stored therein.

Non-transitory memory 206 may further store a training module 212, which may comprise instructions for training one or more of the ML models stored in motion detection module 208 and/or reconstruction module 210. Training module 212 may include instructions that, when executed by processor 204, cause image processing system 202 to conduct one or more of the steps of a training method for training the reconstruction model to reconstruct images from motion-affected k-space data, as discussed in more detail below in reference to FIG. 4 and FIG. 9. In some embodiments, training module 212 may include instructions for implementing one or more gradient descent algorithms, applying one or more loss functions, and/or training routines, for use in adjusting parameters of one or more ML models of motion detection module 208 and/or reconstruction module 210. Training module 212 may include training datasets for the one or more ML models of motion detection module 208 and/or reconstruction module 210.

Non-transitory memory 206 further stores k-space/image database 214. K-space/image database 214 may include, for example, k-space data acquired via an MRI system and images reconstructed from the k-space data. For example, k-space/image database 214 may store k-space data acquired via MRI apparatus 10, and/or received from other communicatively coupled MRI systems or image databases. In some examples, k-space/image database 214 may store images reconstructed by reconstruction module 210. K-space/image database 214 may further include one or more training datasets for training the one or more ML models of motion detection module 208 and/or reconstruction module 210.

In some embodiments, non-transitory memory 206 may include components disposed at two or more devices, which may be remotely located and/or configured for coordinated processing. In some embodiments, one or more aspects of non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of k-space data to use in training a machine learning model, or for further processing using a trained machine learning model (e.g., the reconstruction model disclosed herein).

Display device 234 may include one or more display devices utilizing virtually any type of technology. In some embodiments, display device 234 may comprise a computer monitor, and may display MR images, including images reconstructed by reconstruction module 210. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view MRI images produced by an MRI system, and/or interact with various data stored in non-transitory memory 206.

It should be understood that image processing system 202 shown in FIG. 2 is for illustration, not for limitation. Another appropriate image processing system may include more, fewer, or different components.

FIG. 3 schematically shows a process 300 for reconstructing images from motion-affected k-space data, which may be performed by the image processing system 202 of FIG. 2. The process 300 may include detecting one or more echo trains with a specified echo train length (ETL) in the multi-ETL k-space which are affected by motion. Each echo train may result in MR signals that fill a subset of k-space. For example, an echo train having an ETL of 8 may fill 8 k-space lines. If motion is detected in that echo train, each k-space line filled by that echo train may be motion-affected and thus referred to as a motion-affected ETL. Once each motion-affected echo train, and hence each motion-affected ETL is detected, the process may include removing the motion-affected k-space ETLs and performing a deep learning (DL)-based reconstruction of an MR image after removal of the motion-affected k-space ETLs using a reconstruction model (e.g., the reconstruction model stored in the reconstruction module 210) trained to reconstruct images for arbitrary missing k-space lines. Thus, as used herein, the term "k-space ETL" or "ETL of k-space" may refer to the k-space data filled during an echo train having more than one echo. Each ETL of a given k-space dataset may comprise multiple lines of k-space (e.g., 8, 16, etc.)

More specifically, the process may include inputting motion-affected k-space data 302 usable to generate an image into a motion detection model 304, which may output an indication of which ETLs of the motion-affected k-space data 302 are affected by motion, shown schematically as detected motion-affected ETLs 306. As explained above, the motion-affected k-space data 302 may be acquired via multiple echo trains each having a specified length (e.g., number of echoes). For example, each line of k-space may be acquired from a respective echo. The detected motion-affected ETLs 306 may include motion-affected k-space ETLs each comprising a respective plurality of k-space lines (e.g., white regions) and non-motion-affected k-space ETLs each comprising a respective plurality of k-space lines (e.g., black regions). In other embodiments, the motion-affected ETLs of k-space may be detected by alternative mechanisms, including by using analytical methods or based on output received from one or more sensors of an MRI system (e.g., one or more cameras).

A complimentary mask may be generated at 308 based on the detected motion-affected ETLs 306 of the motion-affected k-space data 302. The complimentary mask may be a binary mask 310 wherein the binary mask 310 includes regions being removed (e.g., being masked) from the motion-affected k-space data 302 (e.g., black regions) and regions not being removed (e.g., white regions) from the motion-affected k-space data 302. In some embodiments, mask pixel values of 1 (e.g., visually distinguished as black pixels in binary mask 310) may indicate the presence of motion-affected k-space ETLs/lines and mask pixel values of 0 (e.g., visually distinguished as white pixels in binary mask 310) may indicate the presence of non-motion-affected k-space ETLs/lines. The binary mask 310 may be applied to the motion-affected k-space 302 to remove the detected motion-affected ETLs 306 and generate zero-filled k-space data 312 (also referred to herein as undersampled k-space data). The zero-filled k-space data 312 includes the non-motion-affected ETLs/lines of the motion-affected k-space data 302. In other words, the zero-filled k-space data 312 includes the k-space data of motion-affected k-space data 302 remaining after the motion-affected k-space ETLs are removed. Further, in some examples, a dominant pose may be identified based on the detected motion-affected ETLs 306 and the complimentary mask may be generated to remove the k-space ETLs/lines corresponding to any non-dominant poses, even if such ETLs/lines are not motion-affected. Additional details about identification of the dominant pose are provided below with respect to FIG. 8.

The zero-filled k-space data 312 may be entered as input to a reconstruction model. In the example shown in FIG. 3, the reconstruction model is an unrolled reconstruction DL model 314. A reconstructed image 316 may be outputted from the unrolled reconstruction DL model 314 responsive to the zero-filled k-space data 312 being input into the unrolled reconstruction DL model 314. The unrolled reconstruction DL model 314 may be trained to perform artifact-free reconstruction from an arbitrary number (and placement) of dropped k-space ETLs, as shown by FIG. 4.

Turning to FIG. 4, a process 400 for training a reconstruction model (e.g., the unrolled reconstruction DL model 314) is illustrated. The unrolled reconstruction DL model 314 may be trained to reconstruct images acquired with an MRI system, such as MRI apparatus 10 of FIG. 1, in accordance with one or more operations described in greater detail below in reference to FIG. 9. The process 400 may be implemented by one or more computing systems, such as image processing system 202 of FIG. 2, to train the unrolled reconstruction DL model 314 to reconstruct images acquired with the MRI system based on zero-filled/undersampled k-space data 408 and undersampled images 412. Once trained, the unrolled reconstruction DL model 314 may be used to reconstruct images acquired with an MRI apparatus (e.g., MRI apparatus 10 of FIG. 1) using motion-affected k-space data with motion-affected k-space ETLs, in accordance with one or more operations described in greater detail below in reference to FIG. 8.

The process 400 includes obtaining k-space data 402 of one or more subjects. The k-space data 402 may include a plurality of separate k-space datasets, each sufficient to form a respective image. Each k-space dataset of the k-space data 402 includes a plurality of ETLs, with each ETL comprising a respective plurality of k-space lines. Using a dataset augmentor 404 on the k-space data 402, a plurality of complimentary masks 406 may be generated for each k-space dataset, where each mask acts to randomly remove one or a set of ETLs in k-space (e.g., from 25% to 67% of k-space lines) from a k-space dataset of the k-space data 402. As one example, 62% of k-space lines in a first k-space dataset of the k-space data 402 may be removed. In another example, 33% of k-space lines in a second k-space dataset of the k-space data 402 may be removed. For each number and placement of ETLs to be dropped from a k-space dataset of k-space data 402, a complimentary mask is generated to mask the arbitrary number and placement of ETLs of the k-space data to form undersampled k-space data 408. Each undersampled k-space data 408 may be an undersampled version of the k-space dataset of the k-space data 402. The process 400 includes generating a corresponding undersampled image of undersampled images 412 with transformer 410 using the undersampled k-space data 408. For example, a Fourier transform may be performed on an undersampled version of a k-space dataset to form a corresponding undersampled image.

Thus, for each k-space dataset of the k-space data 402, one or more complimentary masks are applied to mask one or more ETLs of k-space data of the k-space dataset, thereby forming a plurality of different undersampled k-space datasets (collectively forming the undersampled k-space data 408). Each undersampled k-space dataset is generated from a full k-space dataset that includes a complete set of lines of k-space. The complimentary masks are generated so as to mask an arbitrary number and placement of k-space ETLs. In some examples, the minimum number of ETLs that may be removed for a given undersampled k-space dataset may be one ETL comprised of 4, 8, 16, or 32 lines of k-space, for example, while the maximum number of ETLs that may be removed may be based on a minimum amount of k-space to maintain in the undersampled k-space dataset, such as maintaining at least 25% of the k-space data in the k-space dataset. For a given full k-space dataset, a plurality of undersampled k-space datasets may be formed, each with a different number and/or placement of k-space ETLs removed. A plurality of full k-space datasets may be obtained and processed to form the training data as described herein, with the plurality of full k-space datasets obtained from different subjects, of different anatomies, and/or of different MR contrast (e.g., T1, T2, etc.). An undersampled image may be formed from each undersampled k-space dataset. Similarly, a ground truth image may be generated from each full k-space dataset of the k-space data 402.

The process 400 includes generating a plurality of training triads of data using a dataset generator 414. The plurality of training triads of data may be stored in a training module 416. The training module 416 may be the same as or similar to the training module 212 of image processing system 200 of FIG. 2. The plurality of training triads of data may be divided into training triads 418 and test triads 420. Each of training triads 418 and test triads 420 may include an undersampled input image from undersampled images 412, corresponding k-space data of the undersampled input image from undersampled k-space data 408, and a ground truth image based on k-space data of k-space data 402. Thus, a given training triad may include a ground truth image generated from a full k-space dataset, an undersampled k-space dataset generated by masking the full k-space dataset, and an undersampled image generated from the undersampled k-space dataset.

In an embodiment, the dataset generator 414 may pair undersampled images and undersampled k-space data of the k-space data 402 with corresponding ground truth images, where each training triad and/or each test triad of the training triads 418 and the test triads 420, respectively, includes an undersampled image input of undersampled images 412, corresponding undersampled k-space data of undersampled k-space data 408, and a ground truth image based on k-space data of k-space data 402. Additionally, a number of training triads 418 may be assigned to a validation set, to ensure that sufficient training data is available to prevent overfitting, whereby the unrolled reconstruction DL model 314 learns to map features specific to samples of the training set that are not present in the test set.

Once each triad is generated, each triad may be assigned to either the training triads 418 or the test triads 420. In an embodiment, the triad may be assigned to either the training triads 418 or the test triads 420 randomly in a pre-established proportion. For example, the triad may be assigned to either the training triads 418 or the test triads 420 randomly such that 90% of the triads generated are assigned to the training triads 418, and 10% of the image generated are assigned to the test triads 420. Alternatively, the triad may be assigned to either the training triads 418 or the test triads 420 randomly such that 85% of the triads generated are assigned to the training triads 418, and 15% of the triads generated are assigned to the test triads 420. It should be appreciated that the examples provided herein are for illustrative purposes, and triads may be assigned to the training triads 418 dataset or the test triads 420 dataset via a different procedure and/or in a different proportion without departing from the scope of this disclosure.

A number of training triads 418 and test triads 420 may be selected to ensure that sufficient training data is available to prevent overfitting, whereby an initial DL model 421 learns to map features specific to samples of the training set that are not present in the test set. The process 400 includes training the initial DL model 421 on the training triads 418. The process 400 may include a validator 422 that validates the performance of the initial DL model 421 (as the initial DL model is trained) against the test triads 420. The validator 422 may take as input a trained or partially trained DL model (e.g., the initial DL model 421, but after training and update of the DL model has occurred) and a dataset of test triads 420, and may output an assessment of the performance of the trained or partially trained DL reconstruction model on the dataset of test triads 420.

Once the validator 422 determines that the reconstruction model is sufficiently trained, the unrolled reconstruction DL model 314 may be stored in the reconstruction module 210 of FIG. 2. The unrolled reconstruction DL model 314, when deployed, may reconstruct images of a subject based on k-space data acquired with an MRI apparatus wherein motion-affected k-space ETLs and/or k-space ETLs of non-dominant poses of a plurality of poses of the subject are removed. It may be understood that a dominant pose may include a pose in the plurality of poses with a highest number of ETLs belonging to that pose relative to other poses of the plurality of poses (e.g., non-dominant poses). Newly-acquired k-space data of k-space data 402 may be masked based on motion-affected k-space ETLs and entered as input to the unrolled reconstruction DL model 314 to generate the reconstructed images 426. The reconstructed images 426 may be displayed via a display device or saved to memory as described above with respect to FIG. 2.

FIGS. 5-7 illustrate examples of reconstructed images generated from motion-affected k-space data according to the systems and methods described herein. FIGS. 5-7 exhibit varying degrees of motion artifacts due to being obtained with various degrees of motion by a subject. The reconstructed images may be generated with the unrolled reconstruction DL model 314, which is also described below with regards to FIG. 8. Training of the unrolled reconstruction DL model may be performed according to the method described herein with respect to FIG. 9.

Turning to FIG. 5, a first example of images 500 of a subject generated during an image reconstruction process is shown. The images 500 are images generated from MR signals produced according to a T2-Weighted-Fluid-Attenuated Inversion Recovery acquisition protocol (e.g., T2 FLAIR images). The images 500 include a first image 502, a second image 504, a third image 506, a fourth image 508, a fifth image 510, a sixth image 512, and a seventh image 514. The first image 502 is a simulated motion-affected image reconstructed from a motion-affected k-space dataset. The motion-affected k-space dataset may be a simulated dataset generated by replacing or otherwise modifying lines of non-motion-affected k-space to simulate motion of the subject. The second image 504 is an undersampled image generated from an undersampled k-space data set obtained by applying a binary mask 516 to the motion-affected k-space data corresponding to the first image 502 (e.g., to mask/drop motion-affected lines/ETLs of the motion-affected k-space dataset). The third image 506 is a reconstructed image output by a reconstruction model trained as described herein (e.g., using the undersampled k-space dataset as input), and the fourth image 508 is a ground truth image generated from the non-motion-affected k-space dataset.

The fifth image 510 includes a 10× magnification difference image generated by subtracting the first image 502 from the ground truth image (e.g., the fourth image 508) and multiplying each resultant pixel value by 10 to enhance visualization of the differences between the first image 502 and the fourth image 508. The fifth image 510 emphasizes the motion artifacts present in the first image 502. The sixth image 512 includes a 10× magnification difference image generated by subtracting the second image 504 from the ground truth image and multiplying each resultant pixel value by 10). The sixth image 512 emphasizes that artifacts are still present in the second image 504 despite dropping the motion-affected k-space ETLs. The seventh image 514 includes a 10× magnification difference image generated by subtracting the third image 506 from the ground truth image (and multiplying each resultant pixel value by 10). The seventh image 514 emphasizes the motion artifacts present in the third image 506, which are minimal after removing the motion-affected ETLs of the corresponding k-space data and reconstructing the image with the reconstruction model.

FIG. 6 shows a second example of images 600 generated during an image reconstruction process. The images 600 are images generated from MR signals produced according to a T2-weighted Fast Spin Echo acquisition protocol (e.g., T2 FSE images). The images 600 include a first image 602, a second image 604, a third image 606, a fourth image 608, a fifth image 610, a sixth image 612, and a seventh image 614. The first image 602 is a motion-affected image reconstructed from a motion-affected k-space dataset (e.g., where motion was simulated as described above). The second image 604 is an undersampled image generated from an undersampled k-space data set obtained by applying a binary mask 616 to the motion-affected k-space dataset corresponding to the first image 602. The third image 606 is a reconstructed image output by the reconstruction model described herein based on the undersampled k-space dataset, and the fourth image 608 is a ground truth image.

The fifth image 610 includes a 10× magnification difference image formed by subtracting the first image 602 from the fourth image 608 (and multiplying each resultant pixel value by 10). The fifth image 610 emphasizes the motion artifacts present in the first image 602. The sixth image 612 includes a 10× magnification difference image formed by subtracting the second image 604 from the fourth image 608 (and multiplying each resultant pixel value by 10). The sixth image 612 emphasizes that artifacts are still present in the second image 604, despite dropping the motion-affected k-space ETLs. The seventh image 614 includes a 10× magnification difference image formed by subtracting the third image 606 from the fourth image 608 (and multiplying each resultant pixel value by 10). The seventh image 614 emphasizes the motion artifacts present in the third image 606, which are minimal after removing the motion-affected ETLs of the corresponding k-space data and reconstructing the image with the reconstruction model.

FIG. 7 shows a third example of images 700 generated during an image reconstruction process. The images 700 are images generated from MR signals produced according to a T2-weighted Fast Spin Echo acquisition protocol (e.g., T2 FSE images). The images 700 include a first image 702, a second image 704, a third image 706, a fourth image 708, a fifth image 710, a sixth image 712, and a seventh image 714. The first image 702 is a motion-affected image reconstructed from a motion-affected k-space dataset (e.g., where motion was simulated as described above). The first image 702 is more severely affected by motion than the motion-affected images in FIGS. 5 and 6. The second image 704 is an undersampled image generated from an undersampled k-space data set obtained by applying a binary mask 716 to the motion-affected k-space dataset corresponding to the first image 702. The third image 706 is a reconstructed image output by the reconstruction model described herein based on the undersampled k-space dataset, and the fourth image is a ground truth image.

The fifth image 710 includes a 10× magnification difference image formed by subtracting the first image 702 from the fourth image 708 and multiplying each resultant pixel value by 10. The fifth image 710 emphasizes the motion artifacts present in the first image 702. The sixth image 712 includes a 10× magnification difference image formed by subtracting the second image 704 from the fourth image 708 and multiplying each resultant pixel value by 10. The sixth image 712 emphasizes that artifacts are still present in the second image 704, despite dropping the motion-affected k-space ETLs. The seventh image 714 includes a 10× magnification difference image formed by subtracting the third image 706 from the fourth image 708 and multiplying each resultant pixel value by 10. The seventh image 714 emphasizes the motion artifacts present in the third image 706, which are reduced after removing the motion-affected ETLs of the corresponding k-space data and reconstructing the image with the reconstruction model.

FIG. 8 is a flowchart illustrating a method 800 for deploying a reconstruction model (such as the unrolled reconstruction DL model 314 of FIGS. 3 and 4), according to an embodiment of the disclosure. In some embodiments, the reconstruction model may be a deep neural network that is trained on a training dataset in accordance with the procedure described in method 900 of FIG. 9. Method 800 may be implemented with the image processing system 202 of FIG. 2. Method 800 may be carried out according to instructions stored in non-transitory memory and executed by a processor, such as non-transitory memory 206 and processor 204 of image processing system 202 of FIG. 2.

At 802, the method 800 includes obtaining k-space data of a subject for reconstruction of one or more images. The k-space data may be obtained using an MRI apparatus, such as MRI apparatus 10 of FIG. 1. The k-space data may be obtained in a segmented manner and specific order. In particular, the k-space data may comprise a plurality of lines wherein each line corresponds to MR signals obtained during a respective echo of a plurality of echoes (e.g., of an ETL) as specified by the acquisition protocol.

One or more of the k-space ETLs may be motion-affected due to motion of the subject. Consequently, a motion-affected image with undesired artifacts may be generated from the k-space data. Motion of the subject may occur whereby the subject is positioned in a plurality of poses at various points in time during image acquisition. For example, during MR signal acquisition, the subject may be positioned in a first pose for a first time period and the subject may change position during MR signal acquisition to achieve a second pose. After a second time period, the subject may change position to achieve a third pose. Transitioning from the first pose to the second pose and from the second pose to the third pose may result in undesired movement or motion of the subject that may reduce image quality and hinder the ability to determine a correct diagnosis. To increase image quality, the motion-affected ETLs of the k-space data may be dropped to form undersampled k-space data and the undersampled k-space data may be used to reconstruct the image without the undesired artifacts. Further, the k-space ETLs corresponding to any non-dominant poses may also be removed.

At 804, the method 800 includes detecting motion-affected ETLs of k-space data. A motion detection module (e.g., motion detection module 208) of an image processing system may be configured to detect motion in k-space data. In some embodiments, motion-affected ETLs of k-space data may be detected using deep learning model. The motion detection model may be trained in a suitable manner. In one example, the motion detection model may be trained according to a motion scoring method based on motion phase encoding line detection that is expanded to identify motion affected ETLs of the k-space. As explained previously, an ETL of k-space may include a set of lines of k-space filled during a single echo train, with a line of k-space filled following each echo of the echo train. As another example, the motion detection model may be trained on sub-images generated from pairs of ETLs wherein image features of the sub-images differ when motion is present between ETLs. The motion detection model may be configured to output an identification of each motion-affected ETL. In other embodiments, motion-affected ETLs of k-space data may be detected using analytical methods or based on output received from one or more sensors of the MRI system (e.g., one or more cameras)

At 806, the method 800 includes detecting a dominant pose and one or more non-dominant poses of the subject based on the motion-affected ETLs. As described herein, the k-space data may comprise the plurality of lines wherein each line corresponds to an echo of an ETL, for example. K-space lines filled at a specific time period during image acquisition may correspond to the dominant pose whereas k-space lines filled at other time periods may correspond to one or more non-dominant poses of the plurality of poses. The dominant pose may be the pose that the imaging subject held for the longest duration relative to the one or more non-dominant poses. K-space ETLs of the dominant pose may be identified by identifying the one or more motion-affected ETLs of the plurality of ETLs of the k-space data, as explained above, and classifying each ETL of the plurality of ETLs of the k-space data as belonging to one of a plurality of poses based on the one or more motion-affected ETLs.

Specifically, each pose may be defined by the presence of a motion-affected ETL, occurring after a non-motion affected ETL. Said another way, a first ETL before a first motion-affected ETL may be defined as a first pose; a second ETL after the first motion-affected ETL and before a second motion-affected line ETL may be defined as a second pose; and so forth. The dominant pose may be identified as the pose of the plurality of poses with a highest number of ETLs (e.g., lines of k-space) belonging to that pose relative to other poses of the plurality of poses (e.g., the pose with the most lines/ETLs). Additional details about mapping user motion to k-space ETLs to identify a dominant pose are provided below with respect to FIG. 10.

As described above, motion may be introduced into the k-space data when the subject transitions between different poses during image acquisition. By identifying the one or more motion-affected ETLs in the k-space, transitions between the different poses of the plurality of poses may be detected. In one example, a first motion-affected ETL may indicate a transition from a first non-dominant pose to the dominant pose of the plurality of poses. As another example, a second motion-affected ETL may indicate a transition from the dominant pose to a second non-dominant pose of the plurality of poses. In a further example, a third motion-affected ETL may indicate a transition from the second non-dominant pose to a third non-dominant pose of the plurality of poses.

At 808, the method 800 includes identifying ETL(s) of k-space corresponding to non-dominant poses. The different motion-affected ETLs of the k-space data may be separated by one or more non-motion-affected ETLs. The dominant pose may be the non-motion-affected ETL(s) with the highest number of ETLs/lines (that are not motion-affected). The remaining lines/ETLs of the k-space data may correspond to the non-dominant poses of the plurality of poses.

At 810, the method 800 includes outputting a complimentary mask masking the identified ETLs. In some embodiments, the generated complimentary mask may be configured to mask only the motion-affected ETL(s). In other embodiments, the generated complimentary mask may be configured to mask only the ETL(s) corresponding to the non-dominant pose. The generated complimentary mask may be a binary mask that includes regions being removed and regions not being removed from the k-space. As described herein, mask pixel values of 0 may indicate the presence of motion-affected k-space data or non-dominant poses and mask pixel values of 1 may indicate the presence of non-motion affected k-space data or the dominant pose. The regions not being removed may be the ETLs that are not motion-affected and/or correspond to the dominant pose and the regions being removed may be the remaining lines/ETLs of k-space that are motion affected and/or corresponding to one or more non-dominant poses of a plurality of poses.

At 812, the method 800 includes applying the complimentary mask to the k-space data to generate an undersampled k-space dataset. Each undersampled k-space dataset is generated from a respective full k-space dataset by masking one or more ETLs of the full k-space dataset using the complimentary mask. By applying the complimentary mask to the k-space data, the motion-affected ETLs may be removed from the full k-space data in addition to the ETLs corresponding to the one or more non-dominant poses of the subject. In this way, the undersampled k-space (e.g., zero filled k-space data) may include ETLs/lines of the full k-space data that are not motion-affected and correspond to the dominant pose of the subject during image acquisition.

By selecting the dominant pose (e.g., the pose held for the longest time duration and/or with the most k-space lines) for image reconstruction and removing the one or more non-dominant poses and/or motion-affected k-space ETLs, spatial data variation due to motion is reduced. In other words, medical images generated using the dominant pose without motion corruption may ensure that the imaged anatomy is located in the same position in the entire slice during imaging, which may enhance motion artifact reduction and enable accurate diagnoses of the subject. In this way, spatial data corruption due to the imaged anatomy being located in a different place before and after movement of the subject is reduced.

At 814, the method 800 includes transforming the undersampled k-space dataset to a corresponding undersampled image. Accordingly, an image (e.g., the corresponding undersampled image) with motion affected MR signals and MR signals corresponding to non-dominant poses removed may be generated. However, the undersampled image may not yield a high-quality diagnostic image due to the missing k-space data.

At 816, the method 800 includes inputting the undersampled k-space dataset and corresponding undersampled image to a reconstruction model. The reconstruction model may be a deep learning model trained with a plurality of training data triads, according to the method of FIG. 9, wherein each training data triad includes the undersampled k-space data missing a set of lines of k-space data corresponding to an ETL, a corresponding training image generated from the undersampled k-space dataset, and a ground truth image based on the full k-space dataset (e.g., without missing the set of lines of k-space data).

At 818, the method 800 includes receiving a reconstructed image without motion corruption as output from the reconstruction model. By entering the undersampled image along with the undersampled version of the k-space data as input to the reconstruction model, a reconstructed image without motion artifacts and based on the dominant pose may be generated and output from the reconstruction model.

At 820, the method 800 includes displaying and/or saving the reconstructed image. The reconstructed image may be displayed using a display device, such as a display device communicatively coupled to an image processing system, which may be the image processing system 202 of FIG. 2. In this way, a medical professional may visually evaluate the content of the reconstructed image and determine a diagnosis based on the content of the reconstructed image. By reconstructing an image without motion artifacts and based on the dominant pose, the medical professional may correctly diagnose the subject more easily since undesired motion artifacts do not diminish the image quality and render the image un-diagnostic. Further the reconstructed image may be stored in memory of the image processing system (e.g., non-transitory memory 206 of FIG. 2) or in an image archive such as a picture archive and communication system to enable a user or the medical professional to access the reconstructed image at a later time. The method 800 then ends.

Referring now to FIG. 9, a flowchart is shown of a method 900 for training a reconstruction model. The reconstruction model may be a non-limiting example of the unrolled reconstruction DL model 314 of the process 400 of FIG. 4, according to an embodiment. In some embodiments, the reconstruction model may be a deep neural network with a plurality of hidden layers. Method 900 may be executed by a processor of an image processing system, such as the image processing system 202 of FIG. 2. Method 900 may be carried out according to instructions stored in non-transitory memory of the image processing system (e.g., in a training module such as the training module 212 of the image processing system 202 of FIG. 2) and executed by a processor of the image processing system (e.g., the processor 204 of image processing system 202 of FIG. 2). The reconstruction model may be trained on training data comprising one or more sets of triads. Each triad of the one or more sets of triads may comprise an undersampled k-space training dataset, a corresponding undersampled training image, and a ground truth image based on a full k-space training dataset, as described below. In some embodiments, the one or more sets of triads may be stored in a k-space/image database of an image processing system, such as the k-space/image database 214 of image processing system 202 of FIG. 2.

At 902, the method 900 includes receiving a plurality of k-space training datasets. The plurality of k-space training datasets may be acquired with an MRI apparatus, such as MRI apparatus 10 of FIG. 1. The plurality of k-space training datasets may be stored in a k-space/image database of an image processing system (e.g., FIG. 2). The plurality of k-space training datasets may represent MR signals obtained of one or more regions of interest of one or more subjects, such as a brain, spine, and the like. The plurality of k-space training datasets may not be motion-affected. In other words, the plurality of k-space training datasets may not include motion-affected k-space ETLs.

At 904, the method 900 includes selecting one k-space training dataset from the plurality of k-space training datasets. Instructions configured, stored, and executed in memory by a processor may cause the processor to randomly select one k-space training dataset from the plurality of k-space training datasets.

At 906, the method 900 includes generating a ground truth image from the selected k-space training dataset. To enable the accuracy of the reconstruction model to be assessed, a ground truth image based on the one k-space training dataset may be reconstructed. In this way, a reconstructed image output by the reconstruction model based on an undersampled k-space training dataset may be compared with the ground truth image to adjust the parameters of the reconstruction model, as explained below.

At 908, the method 900 includes randomly selecting one or more ETLs of the selected k-space training dataset. Instructions may cause the processor to randomly select the one or more ETLs of the selected k-space training dataset. The randomly selected ETLs may range from 25% to 75% of the k-space lines of the full selected k-space training dataset, for example. As one example, the randomly selected k-space ETLs may include 30% of the k-space lines of the full selected k-space training dataset. In another example, the randomly selected k-space ETLs may include 47% of the k-space lines of the full selected k-space training dataset. The number and/or placement of ETLs of the k-space training dataset that are removed may be different for each training k-space dataset of the plurality of training k-space datasets. It will be appreciated that the k-space training dataset may include a plurality of ETLs and that a single ETL of the k-space training dataset may include a plurality of lines of the k-space training dataset (e.g., 4 lines, 8 lines, 16 lines, etc.) that may be distributed non-consecutively across the k-space training dataset.

At 910, the method 900 includes outputting a complimentary mask of the selected k-space training dataset with the selected ETL(s) masked. As described above with respect to FIG. 4, the outputted complimentary mask may be a binary mask wherein the selected ETL(s) are masked. The binary mask includes regions being removed and regions not being removed from the full k-space training dataset. The masked ETL(s) may be removed from the full k-space training dataset whereas unmasked ETLs may not be removed from the full k-space training dataset.

At 912, the method 900 includes applying the complimentary mask to the selected k-space training dataset to generate an undersampled k-space training dataset. By applying the complimentary mask to the selected k-space training dataset, the randomly selected ETL(s) may be removed from the selected k-space training dataset to form an undersampled k-space training dataset missing lines corresponding to the randomly selected ETL(s). The undersampled k-space training dataset (or zero-filled k-space) may include fewer filled lines than the full k-space training dataset.

At 914, the method 900 includes transforming the undersampled k-space training dataset to a corresponding undersampled training image. The undersampled k-space training dataset may be transformed to generate a corresponding undersampled training image using a Fourier transform on the undersampled k-space training dataset. The undersampled training image does not include image data corresponding to the randomly selected ETL(s). As such, the undersampled training image excludes image data included in the reconstructed ground truth image described above, since the reconstructed ground truth image is generated using the full selected k-space training dataset.

At 916, the method 900 includes inputting the undersampled k-space training dataset and the corresponding undersampled training image to an untrained or partially trained reconstruction model. In some example, the reconstruction model may be an unrolled model. An unrolled reconstruction model may "unroll" iterative MR reconstruction, techniques based on physics-driven DL methods, DL is used as a regularizer and data consistency step is present to ensure physics of image reconstruction is followed. Data consistency can be among methods discussed in the literature such as proximal mapping, ADMM, etc. Instructions configured, stored, and executed in a training module by one or more processors of the image processing system described above with respect to FIG. 4 may cause the undersampled k-space training dataset and corresponding undersampled training image to be entered as input into the reconstruction model.

At 918, the method 900 includes receiving a reconstructed training image output from the reconstruction model. The reconstructed training image output may be a reconstruction of the image of the full selected k-space where MR data associated with the selected ETL(s) is excluded during reconstruction. The reconstructed training image output differs from the corresponding undersampled training image generated from the undersampled k-space dataset. In particular, as the reconstruction model is trained, the reconstructed training image output may be a more refined and higher quality image than the corresponding undersampled training image. In some cases, the corresponding undersampled training image may include a higher degree of undesired artifacts due to the missing image data (or k-space data) than the reconstructed image.

At 920, the method 900 includes comparing the ground truth image with the reconstructed training image and adjusting model parameters of the reconstruction model via backpropagation. Instructions configured, stored, and executed in the training module of the image processing system may compare the ground truth image with the reconstructed training image to calculate a loss function that is used to adjust the model parameters. As mentioned herein, the ground truth image does not include undesired artifacts due to motion affected k-space lines/ETLs. To minimize differences between the ground truth image and the reconstructed training image output from the reconstruction model, a loss function may be calculated based on the reconstructed training image and the ground truth image and used to back propagate adjustments of the untrained or partially trained reconstruction model (e.g., adjust weights, biases, etc.). The loss function may be mean squared error or another suitable loss function.

At 922, the method 900 includes determining whether there are additional k-space training datasets of the plurality of k-space training datasets remaining. In some embodiments, a total number of k-space training datasets of the plurality of k-space training datasets stored in a k-space/image database may be determined with the training module at the beginning of an epoch. Instructions configured, stored, and executed in the training module by the processor may cause the processor to determine the number of k-space training datasets that are undersampled and input into the reconstruction model. In this way, the training module may monitor the number of k-space training datasets that are used to train the reconstruction model compared to the total number of k-space training datasets.

Responsive to determining there are additional k-space training datasets of the plurality of k-space training datasets remaining, the method 900 includes selecting another k-space training dataset from the plurality of k-space training datasets at 904 and dropping one or more ETLs of the selected k-space training dataset to generate an undersampled k-space training dataset and corresponding undersampled training image that is input into the reconstruction model to generate a reconstructed training image to be compared with the ground truth image of the full selected k-space training dataset until there are no remaining k-space training datasets.

In some embodiments, the reconstruction model may be trained on the same k-space training dataset for a number of iterations. For example, during a first iteration, a first ETL or set of ETLs may be dropped from the k-space dataset to form a first undersampled k-space dataset. During a second iteration, a second ETL or set of ETLs may be dropped from the same k-space dataset to form a second undersampled k-space dataset, and so forth. In this way, the reconstruction model may be trained to reconstruct images with a varying number and placement of ETLs that are removed. In this way, a number of initial full k-space datasets demanded for model training may be reduced. Responsive to determining there are no additional k-space datasets of the plurality of k-space datasets, the method 900 then returns.

Thus, the embodiments disclosed herein may reconstruct images from motion-affected MR data using a reconstruction model trained with undersampled k-space data. Motion may occur when a subject transitions between poses, including a dominant pose and/or one or more non-dominant poses. Consequently, motion of the subject may affect and corrupt k-space data acquired during an acquisition protocol and render the reconstructed image non-diagnostic. Diagnosing the subject based on motion-affected k-space data and a corresponding motion-affected image may result in incorrect or missed diagnoses. In some cases, the acquisition protocol may be repeated to acquire uncorrupted k-space data, which may increase a total time duration of the image acquisition protocol and costs associated with imaging the subject.

Instead of repeating the acquisition protocol to obtain uncorrupted k-space data, a reconstruction model, which may be an unrolled reconstruction model or other suitable model, may be trained to reconstruct images based on an undersampled k-space dataset. The undersampled k-space dataset includes k-space lines that are remaining after motion-affected k-space ETLs and k-space ETLs associated with the one or more non-dominant poses have been removed from a full k-space dataset. In this way, an image may be reconstructed based on a dominant pose without significant motion corruption, the dominant pose being the pose of the plurality of poses wherein the subject remains for the longest duration of time.

Since the reconstructed image is based on the dominant pose without motion-affected k-space ETLs, higher quality images without undesired motion artifacts may be generated during the image reconstruction process. In part, the lack of undesired motion artifacts in a reconstructed image may be due to the anatomical regions of interest being located in the same position for a longer time duration (e.g., due to being positioned in the dominant pose) in addition to motion-affected k-space ETLs being removed prior to reconstruction. Additionally, by deploying the reconstruction model, the total time duration of the image acquisition protocol may be reduced as well as the costs associated with the imaging process since the image acquisition protocol is not repeated when motion-affected k-space data is collected.

FIG. 10 schematically shows an example process 1000 for generating an MR image from motion-affected k-space data according to embodiments of the disclosure. Process 1000 may be carried out according to method 800, using a reconstruction model 1016 trained according to method 900.

FIG. 10 illustrates that a patient 1001 being imaged via an MRI apparatus may exhibit motion and thus exhibit two poses during the imaging scan. Specifically, the patient 1001 may exhibit a first pose 1002 and a second pose 1006, with motion occurring during a transition 1004 between the first pose 1002 and the second pose 1006. The patient 1001 may be imaged with an acquisition protocol that dictates 16 repetitions of a pulse sequence be carried out to fill 128 lines of k-space for a selected slice, where each pulse sequence includes an echo train having an ETL of 8. The patient 1001 may hold the first pose 1002 for a first period of time during which repetitions 1-12 (TR 1-12) occur. The patient 1001 may move for a second period of time during which repetition 13 (TR 13) occurs. The patient 1001 may hold the second pose 1006 for a third period of time during which repetitions 13-16 (TR 13-16) occur.

Each repetition may include acquisition of MR signals that are stored in k-space 1008, with each line of k-space storing MR signals acquired during a respective echo. For a given echo train, 8 lines of k-space 1008 are filled. In the example shown, the 8 lines are not consecutive lines. Rather, for a first echo train of a first repetition (TR 1), line 1 may be filled, followed by line 17, then line 33, and so forth. The lines filled during TR 1 (e.g., lines 1, 17, 33, etc.) may comprise a first ETL of k-space 1008. For a second echo train of a second repetition (TR 2), line 2 may be filled, followed by line 18, then line 34, etc. The lines filled during TR 2 (e.g., lines 2, 18, 34, etc.) may comprise a second ETL of k-space 1008.

FIG. 10 includes a magnification 1010 of 16 lines k-space 1008 to illustrate the correspondence between TRs, patient poses, and k-space line filling. Of the 16 lines shown by magnification 1010, the first 12 lines (lines 1-12) are filled during repetitions 1-12 when the patient 1001 holds the first pose 1002, and shown as solid gray lines. Line 13 is filled during repetition 13 when the patient 1001 is moving, and shown as a solid black line. Lines 14-16 are filled during repetitions 14-16 when the patient 1001 holds the second pose 1006, and shown as dashed black lines. As mentioned above, in the example shown, the k-space 1008 may include 128 lines, which may be filled as explained above, such that lines 17-32 include 12 lines filled during TR 1-12, one line filled during TR 13, and three lines filled during TR 14-16; lines 33-48 include 12 lines filled during TR 1-12, one line filled during TR 13, and three lines filled during TR 14-16; and so forth. Thus, each set of 16 lines are filled in the manner shown in magnification 1010.

Using a suitable mechanism such as the motion detection model stored in motion detection module 208, each motion-affected ETL of k-space 1008 may be detected, e.g., each line filled during TR 13. All of the ETLs of k-space 1008 filled prior to TR 13 may be classified as belonging to a first pose. All of the ETLs of k-space 1008 filled after TR 13 may be classified as belonging to a second pose. Because the number of lines/ETLs of k-space filled before TR 13 is greater than the number of lines/ETLs of k-space filled after TR 13 (e.g., 96 lines as opposed to 24 lines), the first pose may be classified as the dominant pose and all lines filled during TR 1-12 (e.g., the first 12 ETLs) may classified as lines belonging to the dominant pose.

A mask 1012 is generated that includes pixel values of 1 for the lines/ETLs of k-space classified as belonging to the dominant pose (depicted in white in mask 1012) and pixel values of 0 for the remaining lines/ETLs of k-space (depicted in black in mask 1012). Thus, the lines of k-space filled while the patient was moving will be masked via mask 1012 (e.g., the 13$^{th}$ ETL). Additionally, the lines of k-space filled while the patient held the second pose will also be masked via mask 1012 (e.g., the 14-16th ETLs). The mask 1012 is applied to the k-space 1008 to generate undersampled k-space 1014 whereby the last four lines of each set of 16 lines is removed/masked (e.g., the lines filled during TR 13-16). For example, the mask may be multiplied by the k-space data such that the data in the last four lines of each set of 16 lines are set to a value of zero while all other data in the k-space are maintained at the original values. The undersampled k-space 1014 is entered as input to the reconstruction model 1016, which outputs a reconstructed image 1018 based on the undersampled k-space 1014. While not shown in FIG. 10, it is to be appreciated that in some examples, an undersampled image may be formed from the undersampled k-space 1014 and entered as input along with the undersampled k-space 1014 to the reconstruction model 1016.

Figure 11:
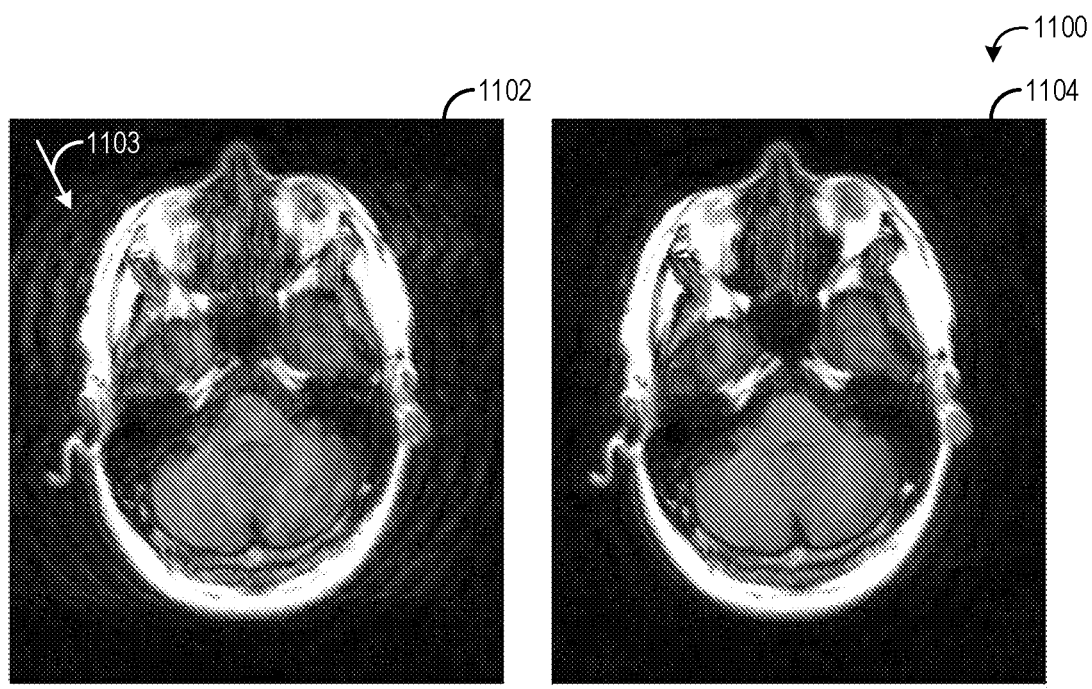
FIGS. 11 and 12 show further example images reconstructed from motion-affected k-space data.
Figure 12:
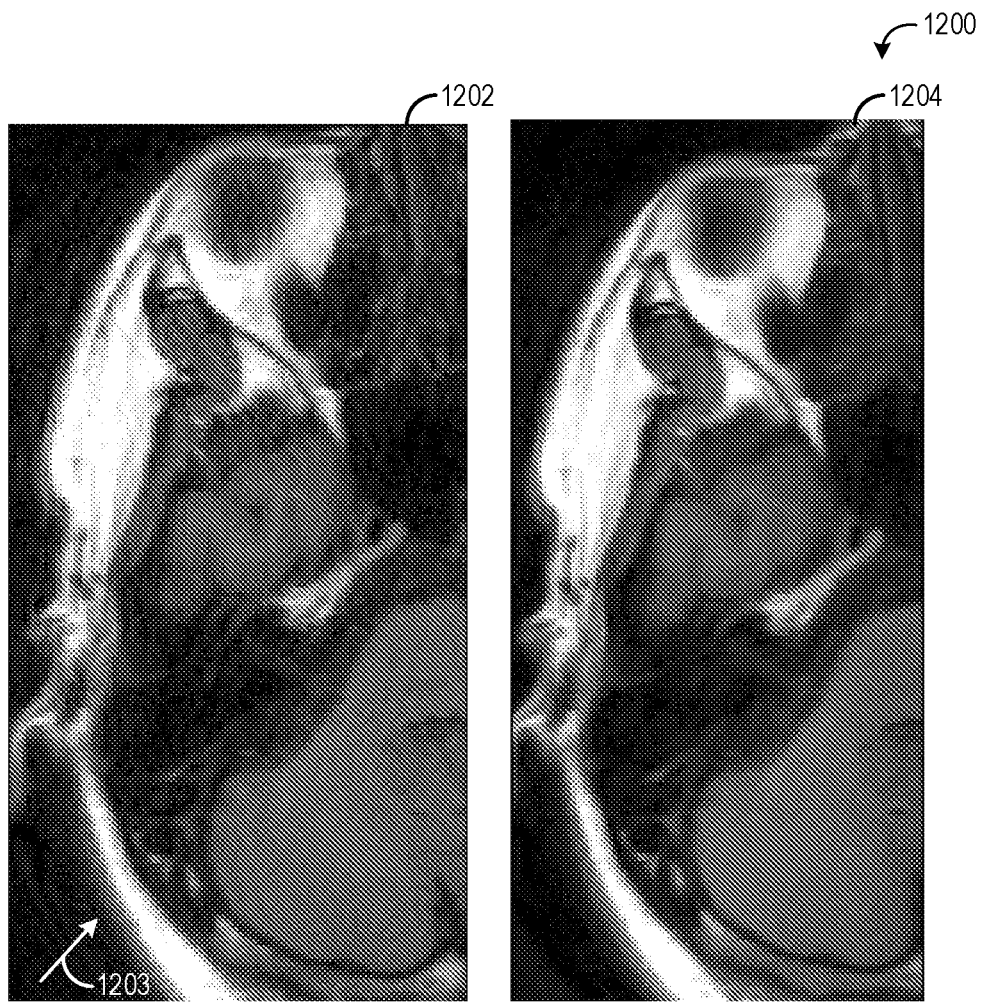

Additional examples of motion-artifact reduction on motion-affected k-space data using the methods described herein are shown in FIGS. 11 and 12. FIG. 11 shows a set of images 1100 including a first image 1102 and a second image 1104. The first image 1102 is reconstructed from motion-affected k-space data, wherein the imaged subject moved a relatively high amount during MR signal acquisition. Motion artifacts present in the first image 1102 may include ghosting artifacts (e.g., shifted repetitions of image features), such as those indicated by arrow 1103. The second image 1104 may be formed by removing the non-dominant pose ETLs of the k-space data as described above with respect to FIGS. 8 and 10 to form undersampled k-space data and reconstructing the second image 1104 using a reconstruction model trained as described above with respect to FIG. 9. The ghosting artifacts are significantly diminished in the second image 1104.

FIG. 12 shows a set of images 1200 including a first image 1202 and a second image 1204. The first image 1202 is reconstructed from motion-affected k-space data, wherein the imaged subject moved a relatively small amount during MR signal acquisition (e.g., less than the motion impacting the first image 1102 of FIG. 11). Motion artifacts present in the first image 1202 may include smearing/blurring artifacts, such as those indicated by arrow 1203. The second image 1204 may be formed by removing the non-dominant pose ETLs of the k-space data as described above with respect to FIGS. 8 and 10 to form undersampled k-space data and reconstructing the second image 1204 using a reconstruction model trained as described above with respect to FIG. 9. The smearing/blurring artifacts are significantly diminished in the second image 1204.

The technical effects of deploying a reconstruction model trained to reconstruct an image based on undersampled k-space data wherein the undersampled k-space data includes image data corresponding to non-motion affected k-space ETLs and/or a k-space ETLs of a dominant pose of the subject is that higher quality reconstructed images without undesired motion artifacts may be obtained, increasing the likelihood of correct diagnoses and decreasing the likelihood of missed diagnoses.

The disclosure also provides support for a method, comprising: obtaining k-space data of a spin echo magnetic resonance imaging (MRI) exam of subject, the k-space data comprising a plurality of echo train lengths (ETLs), each ETL comprising a subset of lines of the k-space data, identifying a subset of ETLs of the plurality of ETLs of the k-space data corresponding to a dominant pose of the subject, generating an undersampled version of the k-space data, the undersampled version including only the subset of ETLs, entering the undersampled version of the k-space data as input to a reconstruction model trained to output a reconstructed image based on the undersampled version of the k-space data, and displaying the reconstructed image on a display device and/or saving the reconstructed image in memory. In a first example of the method, identifying the subset of ETLs of the k-space data corresponding to the dominant pose of the subject comprises identifying the dominant pose by: identifying one or more motion-affected ETLs of the plurality of ETLs of the k-space data, the one or more motion-affected ETLs affected by motion of the subject, classifying each ETL of the plurality of ETLs as belonging to one of a plurality of poses based on the one or more motion-affected ETLs, and identifying the dominant pose as a pose of the plurality of poses with a highest number of ETLs belonging to that pose relative to other poses of the plurality of poses, wherein each ETL classified as belonging to the dominant pose is included in the subset of ETLs. In a second example of the method, optionally including the first example, identifying the one or more motion-affected ETLs comprises entering the k-space data into a motion detection model configured to output an identification of each motion-affected ETL. In a third example of the method, optionally including one or both of the first and second examples, generating the undersampled version of the k-space data comprises: generating a mask configured to mask all ETLs of the k-space data other than the subset of ETLs, and applying the mask to the k-space data to form the undersampled version of the k-space data. In a fourth example of the method, optionally including one or more or each of the first through third examples, the method further comprises: transforming the undersampled version of the k-space data to an undersampled image and entering the undersampled image along with the undersampled version of the k-space data as input to the reconstruction model. In a fifth example of the method, optionally including one or more or each of the first through fourth examples, the reconstruction model is an unrolled reconstruction model trained with a plurality of training data triads, each training data triad including an undersampled k-space dataset missing a set of ETLs of k-space data, a training image generated from the undersampled k-space dataset, and a ground truth image, and wherein each undersampled k-space dataset for each training iteration is missing a different set of ETLs. In a sixth example of the method, optionally including one or more or each of the first through fifth examples, each undersampled k-space dataset is generated from a respective full k-space dataset by masking one or more ETLs of the respective full k-space dataset, and wherein each ground truth image is generated from the respective full k-space dataset.

The disclosure also provides support for a system, comprising: one or more processors, and memory storing instructions executable by the one or more processors to: obtain k-space data of a subject, the k-space data comprising a plurality of echo train lengths (ETLs) each comprising a plurality of lines of the k-space data, detect one or more ETLs of the plurality of ETLs affected by motion of the subject, identify a dominant pose of the subject based on the one or more ETLs of the k-space data affected by motion of the subject, identify a subset of ETLs of the k-space data corresponding to the dominant pose, generate an undersampled version of the k-space data, the undersampled version including only the subset of ETLs, enter the undersampled version of the k-space data as input to an unrolled reconstruction model trained to output a reconstructed image based on the undersampled version of k-space data, and display the reconstructed image on a display device and/or save the reconstructed image in memory. In a first example of the system, detecting one or more ETLs of the plurality of ETLs affected by motion of the subject comprises detecting one or more ETLs of the plurality of ETLs affected by motion of the subject via one of entering the k-space data into a trained motion detection model configured to output an identification of each motion-affected ETL or based on output received from one or more sensors configured to detect motion of the subject. In a second example of the system, optionally including the first example, identifying the dominant pose of the subject based on the one or more ETLs of the k-space data affected by motion of the subject comprises classifying each ETL of k-space data as belonging to one of a plurality of poses by identifying one or more ETLs of the k-space data affected by motion separated by one or more ETLs of k-space data not affected by motion. In a third example of the system, optionally including one or both of the first and second examples, identifying the subset of ETLs of the k-space data corresponding to the dominant pose comprises identifying the dominant pose as a pose of the plurality of poses with a highest number of ETLs belonging to that pose relative to other poses of the plurality of poses, wherein each ETL classified as belonging to the dominant pose is included in the subset of ETLs. In a fourth example of the system, optionally including one or more or each of the first through third examples, generating the undersampled version of the k-space data comprises generating a mask based on the one or more ETLs of k-space data affected by motion of the subject and/or one or more non-dominant poses of the plurality of poses and masking the one or more ETLs affected by motion of the subject and/or each ETL classified as belonging to the one or more non-dominant poses of the plurality of poses. In a fifth example of the system, optionally including one or more or each of the first through fourth examples, the instructions are further executable to enter a corresponding undersampled image as input to the unrolled reconstruction model, wherein the corresponding undersampled image is generated by transforming the undersampled version of the k-space data.

The disclosure also provides support for a method, comprising: obtaining k-space data of a subject, the k-space data acquired with a magnetic resonance imaging (MRI) system according to an acquisition protocol and including a plurality of echo train lengths (ETLs), each ETL comprising a respective plurality of lines of the k-space data, detecting one or more ETLs of the k-space data affected by motion of the subject, in response to the detecting, identifying a dominant pose of the subject during execution of the acquisition protocol, identifying a subset of ETLs of the k-space data corresponding to the dominant pose, generating a mask configured to mask all ETLs of the k-space data other than the subset of ETLs corresponding to the dominant pose, applying the mask to the k-space data to form zero-filled k-space data, transforming the zero-filled k-space data to generate a corresponding image, entering the zero-filled k-space data and corresponding image as input to an unrolled reconstruction deep learning (DL) model trained to output a reconstructed image based on the zero-filled k-space data, and displaying the reconstructed image on a display device and/or saving the reconstructed image in memory. In a first example of the method, the unrolled reconstruction DL model is trained on a plurality of training data triads, each training triad comprising training zero-filled k-space data, a corresponding training image of the training zero-filled k-space data, and a ground truth image. In a second example of the method, optionally including the first example, training of the unrolled reconstruction DL model comprises: obtaining a plurality of training k-space datasets based on one or more subjects, each training k-space dataset corresponding to one subject, selecting one training k-space dataset and removing a selected subset of ETLs of the selected training k-space dataset to form a zero-filled training k-space dataset, the selected subset of ETLs selected randomly, transforming the zero-filled training k-space dataset to generate a corresponding training image, entering the zero-filled training k-space dataset and the corresponding training image as input to the unrolled reconstruction DL model to generate a reconstructed training image, comparing the reconstructed training image to a ground truth image, and adjusting model parameters of the unrolled reconstruction DL model based on a comparison of the reconstructed training image and the ground truth image. In a third example of the method, optionally including one or both of the first and second examples, the ground truth image is generated from the selected training k-space dataset. In a fourth example of the method, optionally including one or more or each of the first through third examples, the selected subset of ETLs of the selected training k-space dataset is different for each training k-space dataset of the plurality of training k-space datasets. In a fifth example of the method, optionally including one or more or each of the first through fourth examples, removing the selected subset of ETLs of the selected training k-space dataset comprises generating a training mask configured to mask all ETLs of the selected training k-space dataset other than the selected subset of ETLs and applying the training mask to the selected training k-space dataset to form the zero-filled training k-space dataset. In a sixth example of the method, optionally including one or more or each of the first through fifth examples, the dominant pose comprises a subset of ETLs corresponding to a pose of a plurality of poses with a highest number of ETLs belonging to that pose relative to other poses of the plurality of poses, the other poses being one or more non-dominant poses.

As used herein, the term "approximately" is construed to mean plus or minus five percent of the range unless otherwise specified.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
   obtaining k-space data of a spin echo magnetic resonance imaging (MRI) exam of subject, the k-space data comprising a plurality of echo train lengths (ETLs), each ETL comprising a subset of lines of the k-space data;
   identifying a subset of ETLs of the plurality of ETLs of the k-space data corresponding to a dominant pose of the subject;
   generating an undersampled version of the k-space data, the undersampled version including only the subset of ETLs;
   entering the undersampled version of the k-space data as input to a reconstruction model trained to output a reconstructed image based on the undersampled version of the k-space data; and
   displaying the reconstructed image on a display device and/or saving the reconstructed image in memory.

2. The method of claim 1, wherein identifying the subset of ETLs of the k-space data corresponding to the dominant pose of the subject comprises identifying the dominant pose by:
   identifying one or more motion-affected ETLs of the plurality of ETLs of the k-space data, the one or more motion-affected ETLs affected by motion of the subject;
   classifying each ETL of the plurality of ETLs as belonging to one of a plurality of poses based on the one or more motion-affected ETLs; and
   identifying the dominant pose as a pose of the plurality of poses with a highest number of ETLs belonging to that pose relative to other poses of the plurality of poses, wherein each ETL classified as belonging to the dominant pose is included in the subset of ETLs.

3. The method of claim 2, wherein identifying the one or more motion-affected ETLs comprises entering the k-space data into a motion detection model configured to output an identification of each motion-affected ETL.

4. The method of claim 1, wherein generating the undersampled version of the k-space data comprises:
   generating a mask configured to mask all ETLs of the k-space data other than the subset of ETLs; and
   applying the mask to the k-space data to form the undersampled version of the k-space data.

5. The method of claim 1, further comprising transforming the undersampled version of the k-space data to an undersampled image and entering the undersampled image along with the undersampled version of the k-space data as input to the reconstruction model.

6. The method of claim 5, wherein the reconstruction model is an unrolled reconstruction model trained with a plurality of training data triads, each training data triad including an undersampled k-space dataset missing a set of ETLs of k-space data, a training image generated from the undersampled k-space dataset, and a ground truth image, and wherein each undersampled k-space dataset for each training iteration is missing a different set of ETLs.

7. The method of claim 6, wherein each undersampled k-space dataset is generated from a respective full k-space dataset by masking one or more ETLs of the respective full k-space dataset, and wherein each ground truth image is generated from the respective full k-space dataset.

8. A system, comprising:
   one or more processors; and
   memory storing instructions executable by the one or more processors to:
      obtain k-space data of a subject, the k-space data comprising a plurality of echo train lengths (ETLs) each comprising a plurality of lines of the k-space data;
      detect one or more ETLs of the plurality of ETLs affected by motion of the subject;
      identify a dominant pose of the subject based on the one or more ETLs of the k-space data affected by motion of the subject;
      identify a subset of ETLs of the k-space data corresponding to the dominant pose;
      generate an undersampled version of the k-space data, the undersampled version including only the subset of ETLs;
      enter the undersampled version of the k-space data as input to an unrolled reconstruction model trained to output a reconstructed image based on the undersampled version of k-space data; and
      display the reconstructed image on a display device and/or save the reconstructed image in memory.

9. The system of claim 8, wherein detecting one or more ETLs of the plurality of ETLs affected by motion of the subject comprises detecting one or more ETLs of the plurality of ETLs affected by motion of the subject via one of entering the k-space data into a trained motion detection model configured to output an identification of each motion-affected ETL or based on output received from one or more sensors configured to detect motion of the subject.

10. The system of claim 8, wherein identifying the dominant pose of the subject based on the one or more ETLs of the k-space data affected by motion of the subject comprises classifying each ETL of k-space data as belonging to one of a plurality of poses by identifying one or more ETLs of the k-space data affected by motion separated by one or more ETLs of k-space data not affected by motion.

11. The system of claim 10, wherein identifying the subset of ETLs of the k-space data corresponding to the dominant pose comprises identifying the dominant pose as a pose of the plurality of poses with a highest number of ETLs belonging to that pose relative to other poses of the plurality of poses, wherein each ETL classified as belonging to the dominant pose is included in the subset of ETLs.

12. The system of claim 10, wherein generating the undersampled version of the k-space data comprises generating a mask based on the one or more ETLs of k-space data affected by motion of the subject and/or one or more non-dominant poses of the plurality of poses and masking the one or more ETLs affected by motion of the subject and/or each ETL classified as belonging to the one or more non-dominant poses of the plurality of poses.

13. The system of claim 8, wherein the instructions are further executable to enter a corresponding undersampled image as input to the unrolled reconstruction model, wherein the corresponding undersampled image is generated by transforming the undersampled version of the k-space data.

14. A method, comprising:
obtaining k-space data of a subject, the k-space data acquired with a magnetic resonance imaging (MRI) system according to an acquisition protocol and including a plurality of echo train lengths (ETLs), each ETL comprising a respective plurality of lines of the k-space data;
detecting one or more ETLs of the k-space data affected by motion of the subject;
in response to the detecting, identifying a dominant pose of the subject during execution of the acquisition protocol;
identifying a subset of ETLs of the k-space data corresponding to the dominant pose;
generating a mask configured to mask all ETLs of the k-space data other than the subset of ETLs corresponding to the dominant pose;
applying the mask to the k-space data to form zero-filled k-space data;
transforming the zero-filled k-space data to generate a corresponding image;
entering the zero-filled k-space data and corresponding image as input to an unrolled reconstruction deep learning (DL) model trained to output a reconstructed image based on the zero-filled k-space data; and
displaying the reconstructed image on a display device and/or saving the reconstructed image in memory.

15. The method of claim 14, wherein the unrolled reconstruction DL model is trained on a plurality of training data triads, each training triad comprising training zero-filled k-space data, a corresponding training image of the training zero-filled k-space data, and a ground truth image.

16. The method of claim 14, wherein training of the unrolled reconstruction DL model comprises:
obtaining a plurality of training k-space datasets based on one or more subjects, each training k-space dataset corresponding to one subject;
selecting one training k-space dataset and removing a selected subset of ETLs of the selected training k-space dataset to form a zero-filled training k-space dataset, the selected subset of ETLs selected randomly;
transforming the zero-filled training k-space dataset to generate a corresponding training image;
entering the zero-filled training k-space dataset and the corresponding training image as input to the unrolled reconstruction DL model to generate a reconstructed training image;
comparing the reconstructed training image to a ground truth image; and
adjusting model parameters of the unrolled reconstruction DL model based on a comparison of the reconstructed training image and the ground truth image.

17. The method of claim 16, wherein the ground truth image is generated from the selected training k-space dataset.

18. The method of claim 17, wherein the selected subset of ETLs of the selected training k-space dataset is different for each training k-space dataset of the plurality of training k-space datasets.

19. The method of claim 16, wherein removing the selected subset of ETLs of the selected training k-space dataset comprises generating a training mask configured to mask all ETLs of the selected training k-space dataset other than the selected subset of ETLs and applying the training mask to the selected training k-space dataset to form the zero-filled training k-space dataset.

20. The method of claim 14, wherein the dominant pose comprises a subset of ETLs corresponding to a pose of a plurality of poses with a highest number of ETLs belonging to that pose relative to other poses of the plurality of poses, the other poses being one or more non-dominant poses.

* * * * *